(12) United States Patent
Datla et al.

(10) Patent No.: US 8,389,551 B2
(45) Date of Patent: Mar. 5, 2013

(54) OPTICAL ENANTIOMERS OF PHENYRAMIDOL AND PROCESS FOR CHIRAL SYNTHESIS

(75) Inventors: Anupama Datla, Maharashtra (IN); Pramod Abaji Walavalker, Maharashtra (IN); Ashok Konda, Maharashtra (IN); Sreenath Babunath Trivikram, Maharashtra (IN)

(73) Assignee: Fermenta Biotech (UK) Limited, London (GB)

( * ) Notice: Subject to any disclaimer, the term of this patent is extended or adjusted under 35 U.S.C. 154(b) by 0 days.

(21) Appl. No.: 12/706,171

(22) Filed: Feb. 16, 2010

(65) Prior Publication Data
US 2010/0144799 A1 Jun. 10, 2010

Related U.S. Application Data

(63) Continuation-in-part of application No. 12/301,710, filed as application No. PCT/GB2007/050279 on May 21, 2007, now abandoned.

(30) Foreign Application Priority Data

May 23, 2006 (IN) ............................ 778/MUM/2006

(51) Int. Cl.
 *A61K 31/4402* (2006.01)
 *C07D 213/72* (2006.01)
 *A61P 19/02* (2006.01)
 *A61P 21/02* (2006.01)
 *A61P 25/04* (2006.01)

(52) U.S. Cl. ........................................ 514/352; 546/312
(58) Field of Classification Search .................. 514/352; 546/312
See application file for complete search history.

(56) References Cited

U.S. PATENT DOCUMENTS

| 4,168,308 A | 9/1979 | Wretlind et al. |
| 2005/0159604 A1 | 7/2005 | Zhang |

FOREIGN PATENT DOCUMENTS

GB 1229967 4/1971

OTHER PUBLICATIONS

Berge ( Pharmaceutical Salts, Journal of Pharmaceutical Sciences, vol. 66, No. 1, 1977, pp. 1-18.*
PCT International Search Report from the ISA/European Patent Office for Fermenta Biotech (UK) Limited, International Application No. PCT/GB2007/050279, Filed May 21, 2007, Dated Jul. 31, 2007.
PCT Written Opinion for Fermenta Biotech (UK) Limited, International Application No. PCT/GB2007/050279, Filed May 21, 2007, Dated Nov. 23, 2008.
Brenelli, E.C.S. et al., Dec. 1992, "Enantioselective synthesis of (R)-(-)-1-phenylethanolamines using Baker's yeast reduction of some α-substituted methyl phenyl ketones," Indian Journal of Chemistry, 31B: 821-823.
Heitmeier, Donald E. and Gray, Allan P., May 1964, "β-Hydroxyphenethylamino Derivatives of Various Nitrogen Heterocycles," Journal of Medicinal Chemistry 7(3):288-293.
O'Dell, Thomas B., "Pharmacology of Phenyramidol (IN511) with emphasis on analgesic and muscle-relaxant effectors," Annals of the New York Academy of Sciences 86:191-202.
Stålberg, O, et al., Sep. 1998, "The Effect of Conductivity Tuning in Chiral Separations by CE; Using Hydroxypropyl-β-Cyclodextrin in Combination with Tetraalkylammonium Ions," Chromatographia 48(5/6):415-421.
U.S. Office Action, Mar. 3, 2010, Anupama Dalta, U.S. Appl. No. 12/301,710, filed Nov. 20, 2008.
India First Examination Report for Fermenta Biotech (UK) Limited, IN application No. 778/MUM/2006 filed May 23, 2006, Dated Dec. 15, 2011.
India Examination Report for Fermenta Biotech (UK) Limited, IN application No. 778/MUM/2006 filed May 23, 2006, Dated Feb. 18, 2011.
Sakai et al., "Studies on the Muscle Relaxation Effects of Ethyl Loflazepate (CM6912) and Evaluation as an Anti-Anxiety Drug," Japan. J. Pharmacol., 36, 319-328 (1984).
Hosseinzadeh et al., "Anticonvulsant, sedative and muscle relaxant effects of carbenoxolone in mice," BMC Pharmacology 2003, 3:3.

* cited by examiner

*Primary Examiner* — San-Ming Hui
*Assistant Examiner* — Kathrien Cruz
(74) *Attorney, Agent, or Firm* — Kramer & Amado, P.C.

(57) ABSTRACT

The present invention discloses optically pure (R) and (S) Phenyramidol enantiomers and their pharmaceutically acceptable salts, a process for synthesizing such enantiomers by means of a styrene oxide based synthesis, and also a clinical evaluation of (R) and (S) enantiomers of Phenyramidol, their salts and compositions thereof for enhanced/newer therapeutic benefits.

8 Claims, 11 Drawing Sheets

OPTICAL ENANTIOMERS OF PHENYRAMIDOL AND PROCESS FOR CHIRAL SYNTHESIS

CROSS-REFERENCE TO RELATED APPLICATIONS

This is a continuation-in-part application of U.S. Ser. No. 12/301,710, filed Nov. 20, 2008, which is a national stage of International Application No. PCT/GB2007/050279, filed May 21, 2007, which claims the benefit of priority of Indian Application No. 778/MUM/2006, filed May 23, 2006. The entire contents and disclosures of the preceding applications are incorporated by reference into this application.

Throughout this application, various references or publications are cited. Disclosures of these references or publications in their entireties are hereby incorporated by reference into this application in order to more fully describe the state of the art to which this invention pertains.

FIELD OF THE INVENTION

This invention relates to optically pure (R) and (S) Phenyramidol enantiomers and a process for synthesizing the same.

BACKGROUND OF THE INVENTION

Phenyramidol (also known as Fenyramidol or IN 511 or MJ 505) is a drug chemically known as 2-(β-hydroxyphenethyiamino) pyridine of formula I, attributed for its analgesic and muscle relaxant properties.

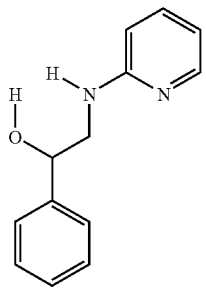

Formula I

The molecular formula for Phenyramidol is $C_{13}H_{14}N_2O$. Preparation of Phenyramidol was first described in 1959 in the Journal of the American Chemical society, indicated for the treatment of several types of pain.

Pain is often classified under various categories e.g. acute and chronic; nociceptive and neuropathic; pain accompanying inflammation (secondary to tissue injury); visceral (smooth muscle) pain and pain (body ache) associated with fever (temperature) etc.

Pain is defined by the International Association for the Study of Pain as an unpleasant sensory and emotional experience associated with actual or potential tissue damage or described in terms of such damage. Under normal circumstances pain is a result of the stimulation of peripheral receptors which transmit impulses to the brain through one or more pain pathways. Early treatment of pain is important as unrelieved pain can have profound psychological effects on the patient.

Opium is one of the most ancient pain relievers known to man. However both the habituation propensity and the addiction potential of opium are well known. The search for safe, effective and non habituating analgesics has been long lasting and continues even today, in the 21st Century. Many drugs pertaining to pure analgesics or analgesics with anti pyretic/anti inflammatory activity; analgesic and muscle relaxant activity etc have been invented with varying degrees of claims of superiority and safety. This range includes NSAIDS, COX-2 inhibitors, Aspirin, Codeine and its derivatives; Morphine and its derivatives, Caffeine and even Corticosteroids to relieve headaches; etc.

Serious side effects, including fatal episodes with COX-2 inhibitors have raised some serious thoughts in the medicinal research community regarding the development of New Chemical Entities (NCEs) for analgesic, anti-inflammatory, muscle relaxant and antipyretic therapeutic applications.

For the past few years, attention has been directed towards the search for new therapeutic indications for existing products and/or towards the examination of already existing old racemic molecules for their isomers of enhanced therapeutic activity.

Phenyramidol (2-{beta-hydroxyphenethylamino}pyridine) introduced originally as an analgesic has shown excellent skeletal muscle relaxant activity at very low doses when used parentally as well as orally. Phenyramidol is unique in its biological effects in that it possesses measurable analgesic and muscle relaxant properties. Of equal importance is the fact that other central effects observed with other analgesics or muscle relaxant drugs (such as sedation, euphoria, and mental confusion) have not been apparent in pharmacological studies of Phenyramidol. The analgesic activity of Phenyramidol is of the order of Codeine and its muscle relaxant activity can abolish abnormal muscle tone without impairing normal neuromuscular function.

The Phenyramidol molecule has an asymmetric carbon (chiral) centre and possesses optical activity. Presently this molecule is used as it is in the form of a 'racemic' mixture and to date no effort has been made to resolve its individual isomers and/or subject them to therapeutic evaluation for existing or new indications.

U.S. Pat. No. 4,168,308 discloses a composition for enhancing parenteral administration comprising a stable, oil-in-water emulsion containing a pharmacologically inert lipid as a hydrophobic phase dispersed in a hydrophilic phase and an effective dose of a pharmacologically active, oil-soluble agent predominantly dissolved in said lipid at a fraction ratio thereto in the hydrophobic phase. The oil-soluble pharmacological agent is a muscle relaxant such as Phenyramidol.

GB 1229967 discloses pharmaceutical compositions for enteral, parenteral and intranasal applications, comprising an oil-soluble therapeutic and/or diagnostic agent dispersed in a diluent comprising an emulsion or dispersion of a pharmaceutically inert lipid and water, at least 50% by weight of the active material being in the lipid phase. Numerous types of medicaments are mentioned and the examples relate to preparations comprising Phenyramidol, hexobarbital, hexyl ether, mecamylamine and quinidine.

Chiral chemistry of all kinds, from kinetic resolution to asymmetric synthesis, chiral chromatographic separation, racemisation and stereochemical inversion, to name a few—have formed the most dynamic subsection of the research activity involved in the development of new chemical entities. There is no relevant and/or useful prior art relating to the (R) and (S) isomers of Phenyramidol or the process for their resolution or for their chiral synthesis in the literature.

In spite of Phenyramidol being a 1959 molecule, no satisfactory chiral synthesis or characterization and therapeutic evaluation of optical enantiomers of Phenyramidol have been reported or attempted to date. There remains a need to accomplish the above objectives to achieve the improved pharmacotherapeutic effects for patient benefit. Therefore the present inventors have met the long felt need in this invention.

SUMMARY OF THE INVENTION

The present invention provides a process for the isolation of substantially pure chiral isomers of Phenyramidol or their salts with an optical purity of above 99%. The invention also provides a clinical evaluation of R (laevo) and S (dextro) enantiomers of Phenyramidol or its salts for enhanced/newer therapeutic benefits and applications.

The present invention discloses optically pure (R) and (S) enantiomers of 2-(β-hydroxyphenethylamino) pyridine, known as phenyramidol of formula I and their pharmaceutically acceptable salts having differentiated and enhanced therapeutic efficacy, for the individual enantiomers and salts thereof.

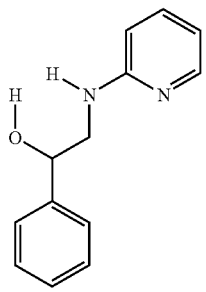

Formula I

According to the present invention, there is provided (R) and (S)-Styrene Oxide based Synthesis for the production of Phenyramidol enantiomers and their salts with high chiral purity. These (R) and (S) enantiomers of Phenyramidol and their salts have been satisfactorily synthesized and characterized for the first time.

According to another aspect, the present invention provides a process for the isolation of substantially pure (R) and (S) isomers of Phenyramidol and their salts with an optical purity of above 99%.

The invention further provides a process for the asymmetric synthesis of (S) Phenyramidol or its pharmaceutically acceptable salts comprising the steps of:

a) reacting 2-aminopyridine with an alkali metal amide in a suitable organic solvent at a temperature of from 55 to 85° C. to obtain the corresponding alkali metal salt of amino pyridine;

b) condensing the alkali metal salt of amino pyridine with (S) styrene oxide at a temperature of from 65 to 90° C.;

c) heating the reaction mass up to about 110° C. with continued stifling for 2 to 3 hrs;

d) isolating the phenyramidol free base from the suitable solvent mixture and e) converting into its pharmaceutically acceptable salt by treating with corresponding acid under conditions effective to form the acid addition salt.

In yet another aspect, the invention provides the process for asymmetric synthesis for preparation of (R) phenyramidol or its pharmaceutically acceptable salts comprising the steps of:

a) reacting 2-aminopyridine with an alkali metal amide in a suitable organic solvent at a temperature of from 55 to 85° C. to obtain the corresponding alkali metal salt of amino pyridine;

b) condensing the alkali metal salt of amino pyridine with (R) styreneoxide at a temperature of from 65 to 90° C.;

c) heating the reaction mass up to about 110° C. with continued stifling for 2 to 3 hrs;

d) isolating the phenyramidol free base from the suitable solvent mixture and e) converting into its pharmaceutically acceptable salt by treating with corresponding acid under conditions effective to form the acid addition salt.

The phenyramidol free base is preferably isolated from water and toluene and may be further crystallized from a suitable solvent, for example a suitable alcoholic solvent, such as methanol.

The alkali metal amide may be selected from the group consisting of sodium amide, potassium amide and lithium amide. The molar ratio of 2-amino pyridine to alkali amide is preferably from about 1:1 to about 1:1.5

The suitable organic solvent used in the reaction is preferably selected from N-methyl-2-pyrollidone (NMP), tetrahydrofuran (THF), dimethyl sulphoxide (DMSO), methyl tert-butyl ether (MTBE), dimethylacetamide (DMA) and dimethylformamide (DMF), the preferred solvent being DMF.

The condensation reaction of the alkali metal salt of amino pyridine with (S) styrene oxide is suitably carried out at a temperature range of from about 65 to about 110° C.

In another aspect, the invention also provides a series of novel salts of phenyramidol enantiomers and the processes for the preparation thereof. The salt-forming groups are selected from groups or radicals having basic or acidic properties. Compounds having a basic group or basic radical, for example a free amino group and compounds having an acidic group or acidic radical, suitable inorganic acids, for example hydrochloric acid, sulfuric acid or a phosphoric acid, or with suitable organic carboxylic acids such as aliphatic, aromatic, di and tri carboxylic acids.

Thus, the process of the invention may further comprise the step of converting the pure enantiomers of phenyramidol free base into their oxalate salts by treating with oxalic acid in a suitable organic solvent or solvent mixture. The suitable solvent is preferably selected from ester solvents such as ethyl acetate, n-butyl acetate, and alcoholic solvents such as methanol, ethanol and isopropanol or combination thereof. The enantiomeric oxalate salts may be crystallized from a solvent selected from alcohols such as methanol, ethanol, isopropanol or combinations thereof, preferably ethyl acetate.

In yet another aspect, the process may further comprise the step of converting the enantiomeric phenyramidol oxalate salts into hydrochloride salts by hydrolyzing the oxalate salt with alkali into free base followed by treating the free base with ethanolic hydrochloride solution to obtain enantiomeric phenyramidol hydrochloride salt.

It is an additional aspect of invention to provide clinical evaluation of (R) and (S) enantiomers of Phenyramidol and their salts for enhanced therapeutic benefits. In accordance with the above aspect, the compounds of the present invention were tested for their pharmacological activity.

In accordance with the above tests, a compound which is a substantially pure (S) isomer of 2-(β-hydroxyphenethylamino) pyridine exhibits enhanced therapeutic effect in management of pain and skeletal muscle relaxant activity.

A compound which is a substantially pure (R) isomer of 2-(β-hydroxyphenethylamino) pyridine exhibits enhanced therapeutic effect in the management of pain and analgesic activity, wherein the activity of the (R) isomer differs from that of the (S) isomer in the range of therapeutic activity.

A substantially pure (R) isomer of 2-(β-hydroxyphenethylamino) pyridine hydrochloride exhibits enhanced analgesic activity, confirmed by an acetic acid induced writhing method. A substantially pure (S) isomer of 2-(β-hydroxyphenethylamino) pyridine hydrochloride salt exhibits enhanced skeletal muscle relaxant activity, confirmed by a Rota-rod method.

The invention further discloses the X-ray crystallographic data of (R) and (S) isomers of the oxalate salts of phenyramidol. Thus, the (S) isomer of 2-(β-hydroxyphenethylamino) pyridine oxalate salt has the X-Ray crystallographic pattern substantially as shown in FIG. 13 and the (R) isomer of 2-(β-hydroxyphenethylamino) pyridine oxalate salt has the X-Ray crystallographic pattern substantially as shown in FIG. 14.

The present invention also provides pharmaceutical compositions which contain salts of phenyramidol and optical enantiomers thereof. It may be important to see the physical and chemical properties of the compound for the inclusion in medicinal agents, and pharmaceutical compositions, etc.

For example, the oxalate salts of (R) and (S) enantiomers of phenyramidol have been tested for their solubility. The oxalate salts have shown poor solubility at room temperature. The hydrochloride salts have shown excellent solubility when compared to oxalate salts. Therefore, the hydrochloride salts facilitate the provision or development of dosage forms from which the drug substance becomes available for bio absorption throughout the GIT. In the light of the above, it has become possible to develop various stable dosage forms to optimize the therapy by improved pharmacokinetic and with pharmacodynamic performance.

Pharmaceutical compositions within the scope of this invention include all the aforesaid novel compounds, wherein the compounds of the present invention are contained in the pharmaceutical composition in an amount effective to achieve its intended performance. Treatment regimens for the administration of the compounds/compositions of the invention can be determined readily by those with ordinary skill in the art. The quantity of the compound and/or composition of the invention administered may vary over a wide range to provide in unit dosage form an effective amount based on the body weight of the patient to achieve the desired effect.

Thus, the invention provides a pharmaceutical composition comprising (R) or (S) isomers of 2-(β-hydroxyphenethylamino) pyridine hydrochloride and pharmaceutically acceptable carriers or excipients useful in the preparation of formulations in treatment of pain or pain related disorders and skeletal muscle disorders and symptoms.

A pharmaceutical composition comprising the (S) isomer of 2-(β-hydroxyphenethylamino) pyridine hydrochloride salt having skeletal muscle relaxant activity and pharmaceutically acceptable carriers or excipients useful to provide relief of spasticity in neuromuscular diseases, such as multiple sclerosis, spinal cord injury, severe head injury, stroke or minor musculo-skeletal injuries is also disclosed in this invention.

A pharmaceutical composition comprising the (R isomer) isomer of 2-(β-hydroxyphenethylamino) pyridine hydrochloride salt having analgesic activity and pharmaceutically acceptable carriers or excipients useful in treating analgesic conditions is also provided by the invention.

DETAILED DESCRIPTION OF THE INVENTION

Figure 1:
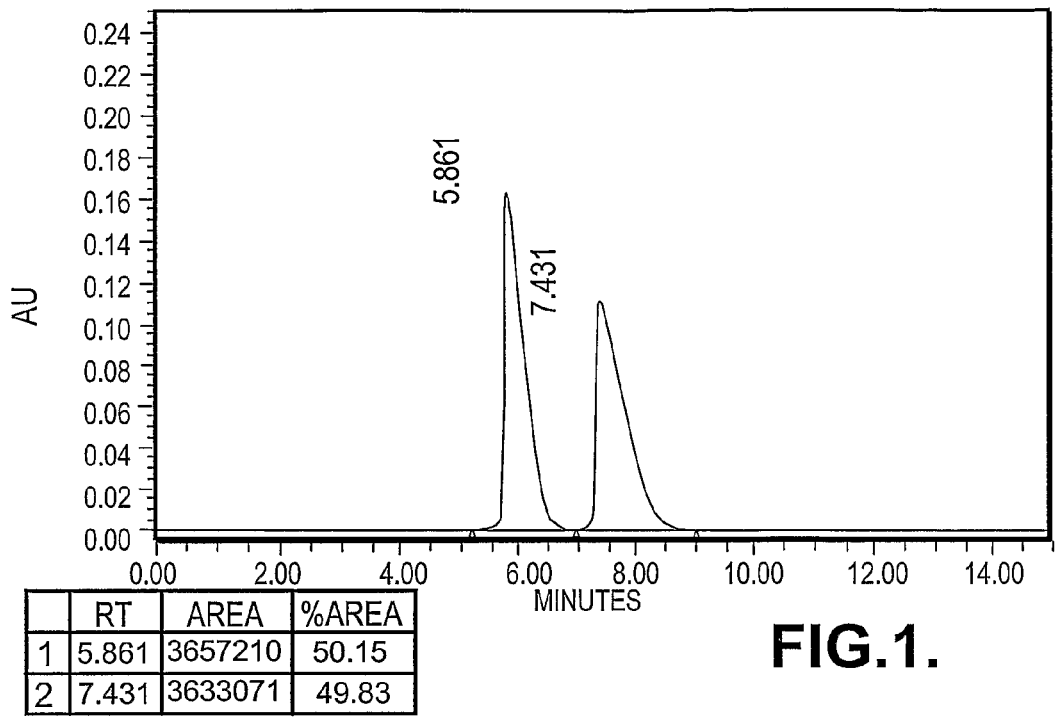
FIG. 1 shows an HPLC chromatogram indicating the resolution of two optical isomers from a racemic mixture of Phenyramidol Hydrochloride.
Figure 2:
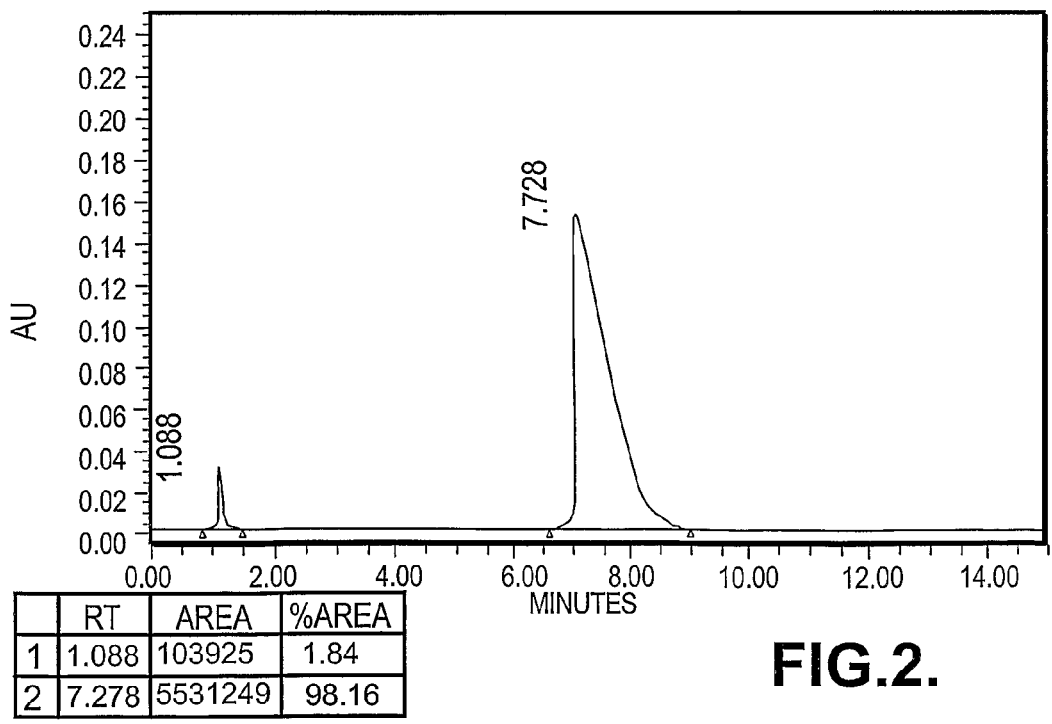
FIG. 2 shows an HPLC chromatogram indicating the peak obtained by the (R) isomer of Phenyramidol Oxalate (the synthesis of which is described in Example 2).
Figure 3:
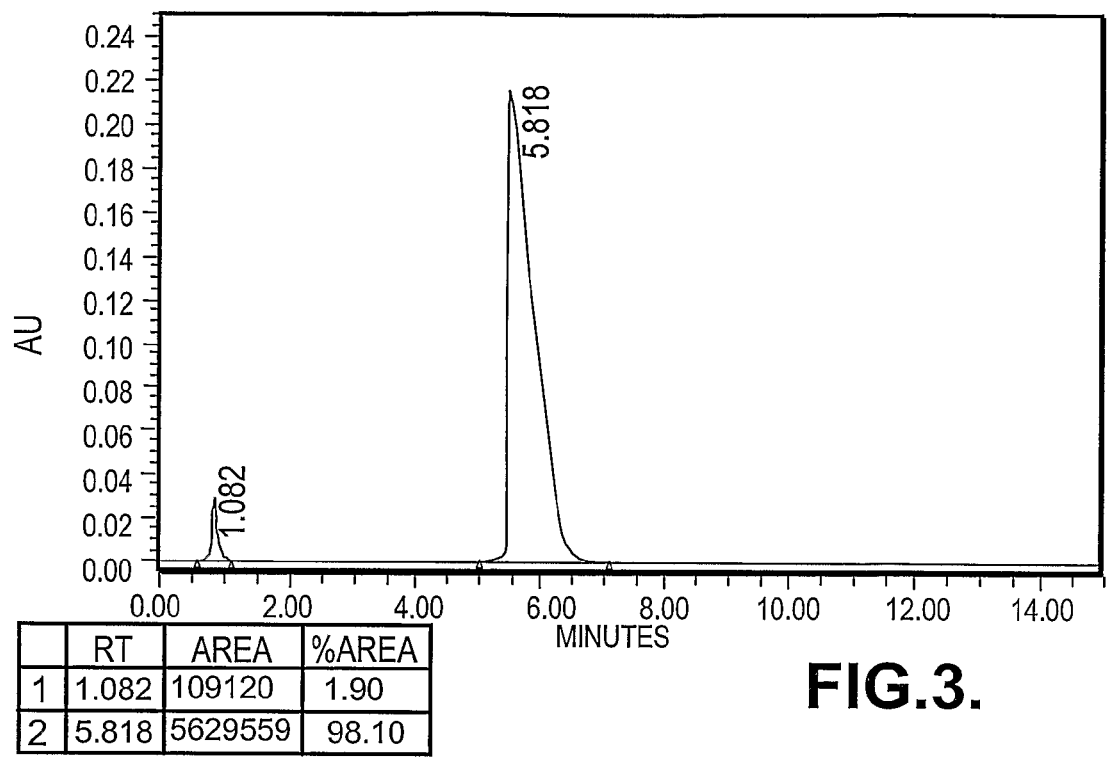
FIG. 3 shows an HPLC chromatogram indicating the peak obtained by the (S) isomer of Phenyramidol Oxalate (the synthesis of which is described in Example 5).
Figure 4:
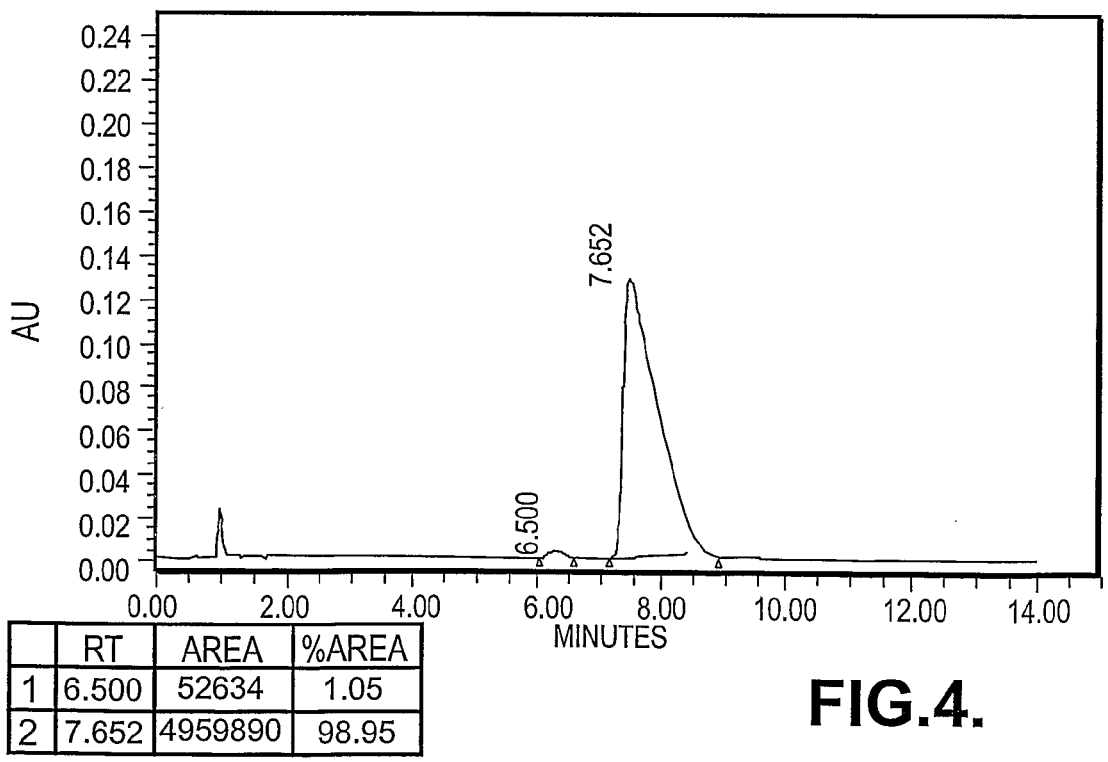
FIG. 4 shows an HPLC chromatogram indicating the peaks obtained by a adding separately 1% (S) isomer to the (R) isomer of Phenyramidol Oxalate.
Figure 5:
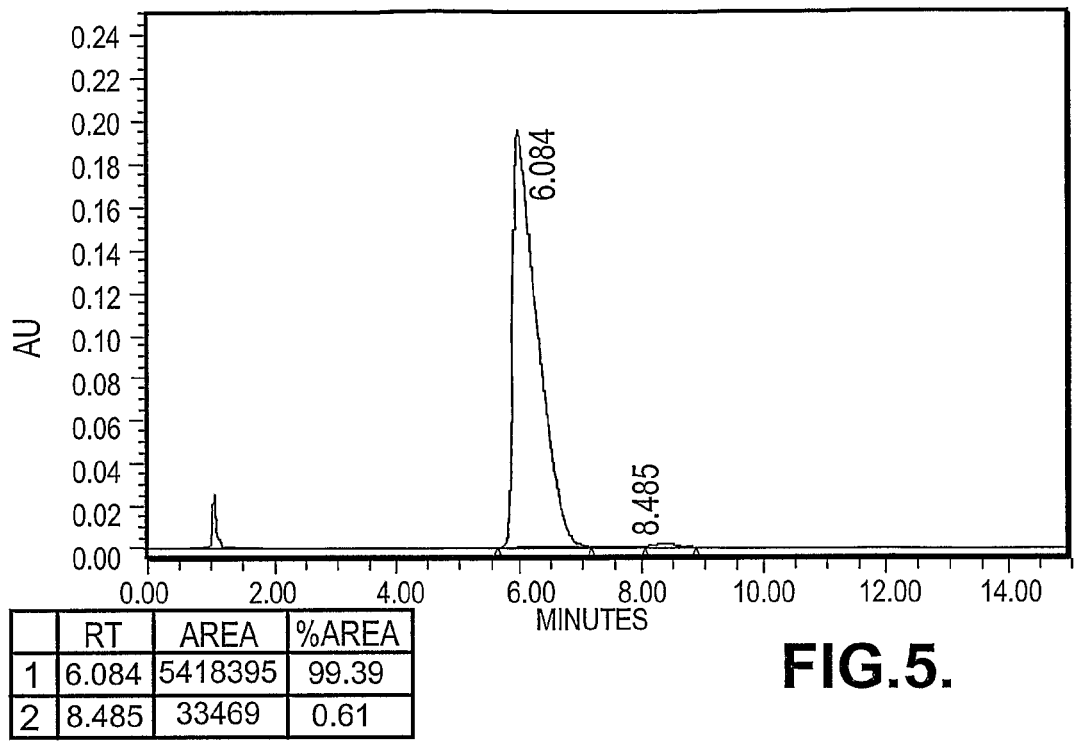
FIG. 5 shows an HPLC chromatogram indicating the peaks obtained by adding separately 1% (R) isomer to the (S) isomer of Phenyramidol Oxalate.
Figure 6:
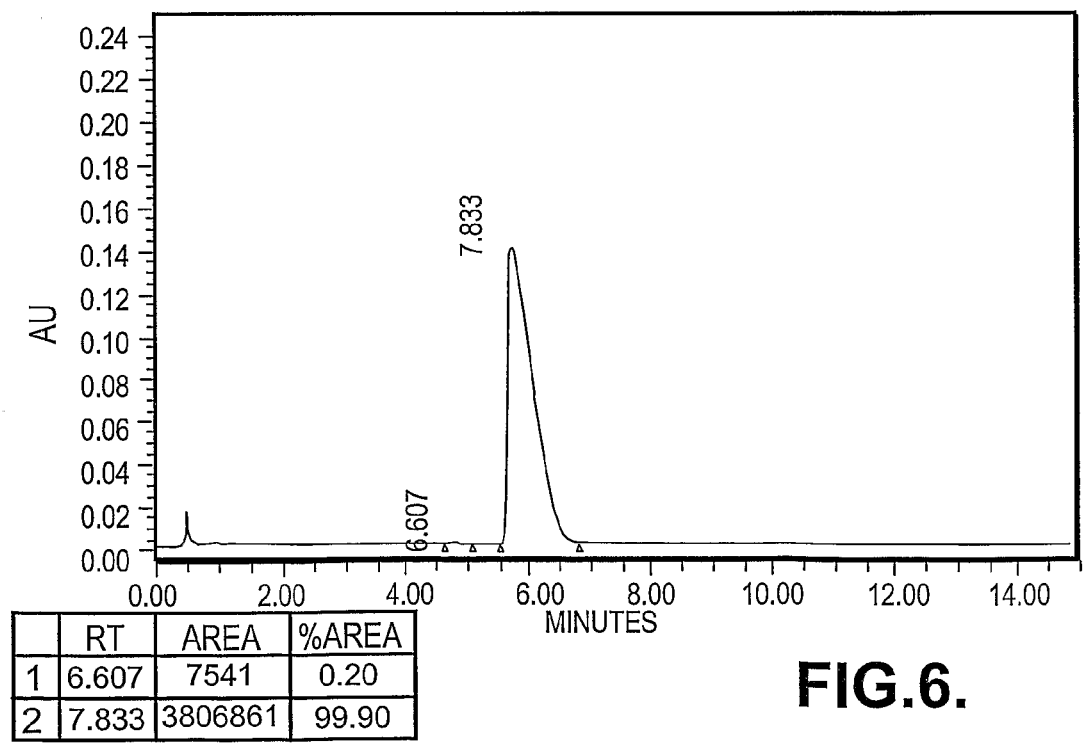
FIG. 6 shows an HPLC chromatogram indicating the peak obtained by the (R) isomer of Phenyramidol free base (which is isolated and converted to hydrochloride salt as indicated in Example 3).
Figure 7:
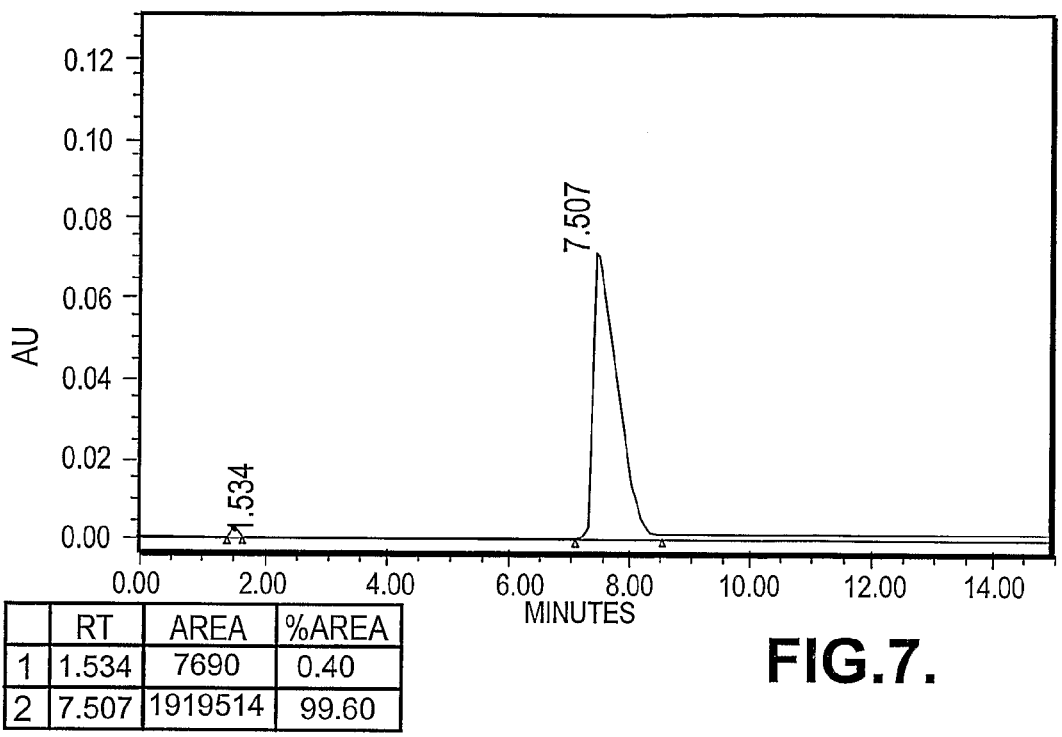
FIG. 7 shows an HPLC chromatogram indicating the peak obtained by the (R) isomer of Phenyramidol Hydrochloride (the synthesis of which is described in Example 3).
Figure 8:
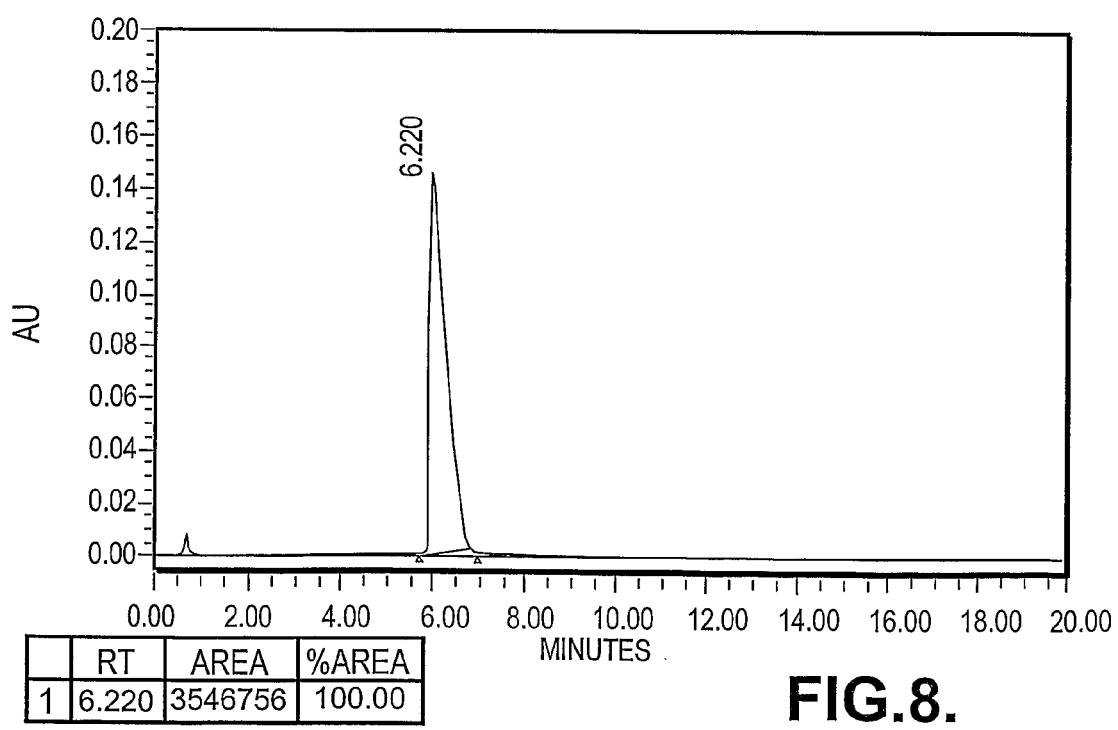
FIG. 8 shows an HPLC chromatogram indicating the peak obtained by the (S) isomer of Phenyramidol free base (which is isolated and converted to hydrochloride salt as indicated in Example 6).
Figure 9:
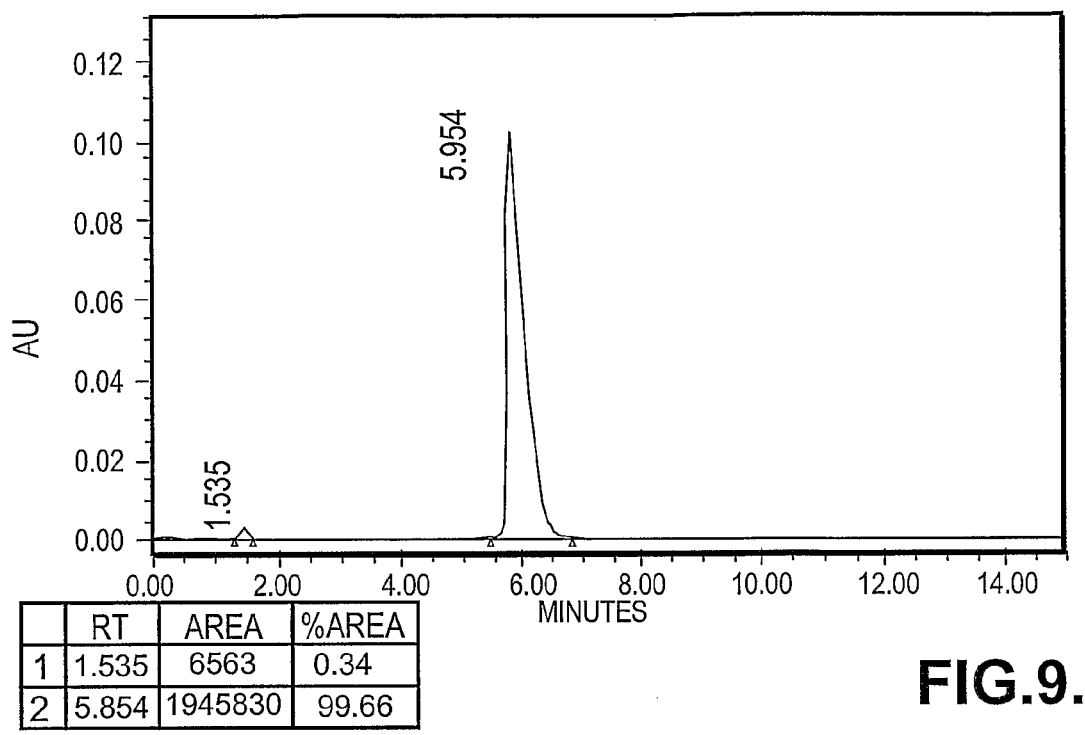
FIG. 9 shows an HPLC chromatogram indicating the peak obtained by the (S) isomer of Phenyramidol Hydrochloride (the synthesis of which is described in Example 6).
Figure 10:
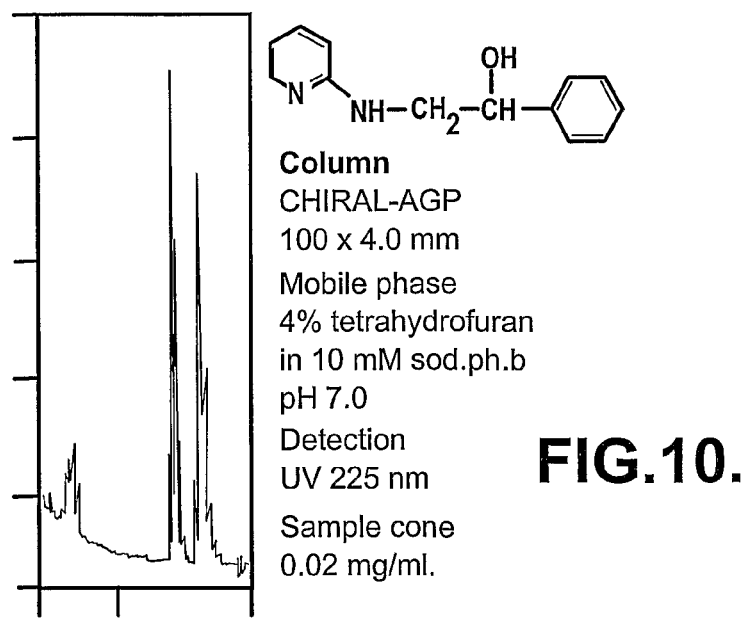
FIG. 10 indicates the resolution of optical isomers of Phenyramidol by HPLC, as reported in the literature. (Column used: $\alpha_1$-acid glycoprotein 100×4.0 mm; Mobile phase: 4% tetrahydrofuran in 10 m/v sodium phosphate buffer pH: 7; Detection: 225 nm; Sample concentration: 0.02 mg/ml.) This Figure is provided as a reference for comparison and validation of this invention.

The invention will now be described in detail in connection with certain preferred and optional embodiments, so that various aspects thereof may be more fully understood and appreciated.

As used herein, the phrase "laevo" refers to the "(R)" enantiomer and the phrase "dextro" refers to the "(S)" enantiomer of phenyramidol or its salts thereof.

In the present invention, (R) and (S) Styrene Oxides are employed in the synthesis of Phenyramidol enantiomers with high chiral purity. The process of the present invention provides advantages such as an effective use of starting materials, minimal formation of undesired product and requirement of milder conditions of operation with less energy consumption and lower pressure. The process described in the present invention makes use of multi-step lab scale processes to ensure cost effective practical manufacturing models to transfer the technology from Lab scale to kilos and to tons of final product thereby providing therapeutic benefits as well as economic cost benefit.

The syntheses of the invention for the production of (R) and (S) phenyramidol salts are illustrated in scheme I and II below:

SCHEME 1

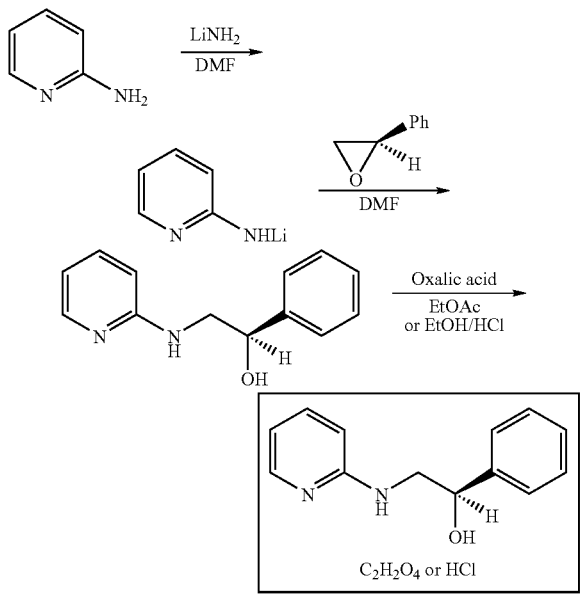

SCHEME 2

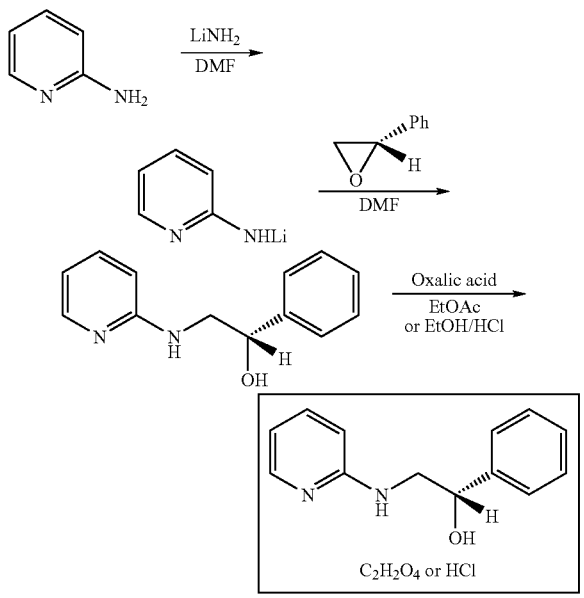

In one embodiment, the invention provides a synthesis for the preparation of substantially pure (S) Phenyramidol, wherein lithiation of 2-aminopyridine is carried out by reacting 2-aminopyridine with an alkali amide in a suitable organic solvent at a temperature of from about 55 to about 85° C. The ammonia gas generated was removed under vacuum at the same temperature. The molar ratio of 2-amino pyridine to alkali amide is from about 1:1 to about 1:1.5 moles.

After completion of the reaction, (S) styrene oxide (1.0-1.5 moles) is added dropwise to the reaction mass at a temperature of from about 65 to about 90° C.; the reaction mass is further heated up to about 110° C. with continued stifling for from about 2 to about 3 hrs until the starting products disappeared (monitored by 15 TLC). The molar range of (S) styrene oxide is from about 1.0 to about 1.5 moles with respect to 2-amino pyridine. The condensation reaction between styrene oxide and the lithium salt of 2-amino pyridine is preferably carried out at a temperature in the range of from about 65 to about 110° C.

After completion of the reaction, the solvent is distilled under reduced pressure. A mixture of toluene and water is added to the reaction mass with stirring at from about 50 to about 70° C. and the product (S) Phenyramidol is separated using a layer separation technique. The crude product, (S) phenyramidol, is crystallized using solvents preferably selected from toluene, benzene, xylene, aqueous methanol or ethanol, and mixtures of two or more thereof, the preferred solvent being methanol.

In another embodiment the invention provides synthesis for the preparation of substantially pure (R) Phenyramidol, wherein lithiation of 2-aminopyridine is carried out by reacting 2-aminopyridine with an alkali amide in a suitable organic solvent at a temperature of from about 55 to about 85° C. The ammonia gas generated was removed under vacuum at the same temperature. The molar ratio of 2-amino pyridine to alkali amide is from about 1:1 to about 1:1.5 moles.

After completion of the reaction, (R) styrene oxide is added dropwise to the reaction mass at a temperature of 65-90° C.; the reaction mass is further heated up to 110° C. with continued stifling for 2 to 3 hrs till the starting products disappeared (monitored by TLC method). The molar range of (R) styrene oxide is 1.0 to 1.5 moles with respect to 2-amino pyridine. The condensation reaction between styrene oxide and lithium salt of 2-amino pyridine is carried out at a temperature range of 65 to 110° C.

After completion of the reaction, the temperature is reduced to 50 to 70° C. and the solvent is distilled under reduced pressure. A mixture of toluene and water is added to the reaction mass with stirring at 50 to 70° C. and separated the product (R) Phenyramidol using layer separation technique. The crude product, (R) phenyramidol is crystallized using solvents selected from toluene, benzene, xylene, aqueous methanol or ethanol, the preferred solvent for crystallization being methanol The organic solvent suitable to perform the above synthesis is preferably selected from the group consisting of N-methyl-2-pyrollidone (NMP), tetrahydrofuran (THF), dimethyl sulphoxide (DMSO), methyl tent-butyl ether (MTBE), dimethylacetamide (DMA) and dimethylformamide (DMF), and suitable mixtures of two or more thereof. DMF is particularly preferred.

The alkali metal amide is preferably selected from sodium amide, potassium amide and lithium amide, most preferably lithium amide.

In yet another embodiment the above prepared (S) or (R) Phenyramidol free bases are converted to their acid addition salts using suitable inorganic acids, for example hydrochloric acid, sulfuric acid or a phosphoric acid, or with suitable organic carboxylic acids such as aliphatic, aromatic, di and tri carboxylic acids. In accordance with this embodiment, (I) Phenyramidol free base is converted into its oxalate salt by treating with oxalic acid in suitable organic solvent and further converted into a hydrochloride salt.

(S) Phenyramidol free base (1 mole) was taken in a suitable solvent and heated at a temperature of 45 to 70° C. Separately oxalic acid (1.0-1.5) was dissolved under heating in the same or different suitable solvent and added to phenyramidol solution. The reaction mass was cooled to room temperature under stirring. The solid separated was filtered and washed with hot solvent and suck dried under vacuum to obtain crude oxalate salt.

The suitable solvent for preparation of oxalate salt is selected from ester solvents such as ethyl acetate, n-butyl acetate, and alcoholic solvents such as methanol, ethanol and isopropanol or combination thereof, the preferred solvent being ethylacetate.

For further purification, the crude (I) oxalate salt is dissolved in a suitable organic solvent and refluxed with activated charcoal for 1 hr, filtered the hot solution over a celite bed and washed with the same solvent. The filtrate is concentrated and cooled to room temperature with stirring. The solid separated is filtered under reduced pressure and washed with ethyl acetate and suck dried under vacuum.

The suitable solvent for crystallization of the crude oxalate salt is selected from alcoholic solvents such as methanol, ethanol, isopropanol or combination thereof, preferably methanol.

Similarly (R) phenyramidol free base is converted into its oxalate salt and further purified by recrystallizing from suitable organic solvent such as methanol by the method described above.

However, oxalate salts of phenyramidol being low soluble in water possesses severe solubility problems. Therefore, oxalate salt is further converted into hydrochloride salt. Phenyramidol hydrochloride salt exhibits higher solubility in water and hence the hydrochloride salt is preferred for further evaluations.

(S)-Phenyramidol Oxalate salt is hydrolyzed with sodium bicarbonate at 20° C. and by stirring at room temperature, solid separated out, which is filtered and refluxed with activated charcoal for 1 hr, filtered the hot solution over celite bed and washed with the same solvent. The solution is concentrated under reduced pressure to get the (S)-phenyramidol free base. The free base is taken in ethanolic hydrochloride solution at 0 to −5° C. and stirred for overnight, the solid separated is filtered and washed with cold ethanol and dried under vacuum.

Similarly, (R)-Phenyramidol Oxalate is converted to its corresponding hydrochloride salt in the optically pure form.

Elemental analysis of (R) and (S)-Phenyramidol Oxalate and hydrochloride salts were carried out at external Laboratory and results are provided in Table 1.

The (R) and (S)-Styrene Oxide based Synthesis of Phenyramidol results in Phenyramidol enantiomers with high chiral purity. The process as per present invention provided with isolation of greater than 99% pure (R) and (S) isomers of Phenyramidol, when studied on laboratory scale.

Purities of the novel compounds arrive at in this invention are as follows:
1. S-Phenyramidol Oxalate—100%
2. R-Phenyramidol Oxalate—100%
3. S-Phenyramidol Hydrochloride—99.6%
4. R-Phenyramidol Hydrochloride—99.66%
5. R-Phenyramidol Free base—99.8%
6. S-Phenyramidol Free base—100%

The advantages of the use of (R) and (S)-Styrene Oxide based Synthesis includes more effective use of starting material, minimal formation of unwanted product and requires milder conditions of operation with less energy consumption and lower pressure requirements. Also, lab scale processes were used to ensure cost effective practical manufacturing models to transfer the technology from Lab scale to kilos and to tons of final product providing therapeutic benefits as well as economic cost benefit.

The oxalate enantiomers of the present invention are subjected to X-ray crystallographic analysis to ascertain the existence of any polymorphy. The experiment was performed on dextro-rotatory crystal and laevo rotatory crystal obtained by recrystallization from demineralized aqueous solution.

Figure 11:
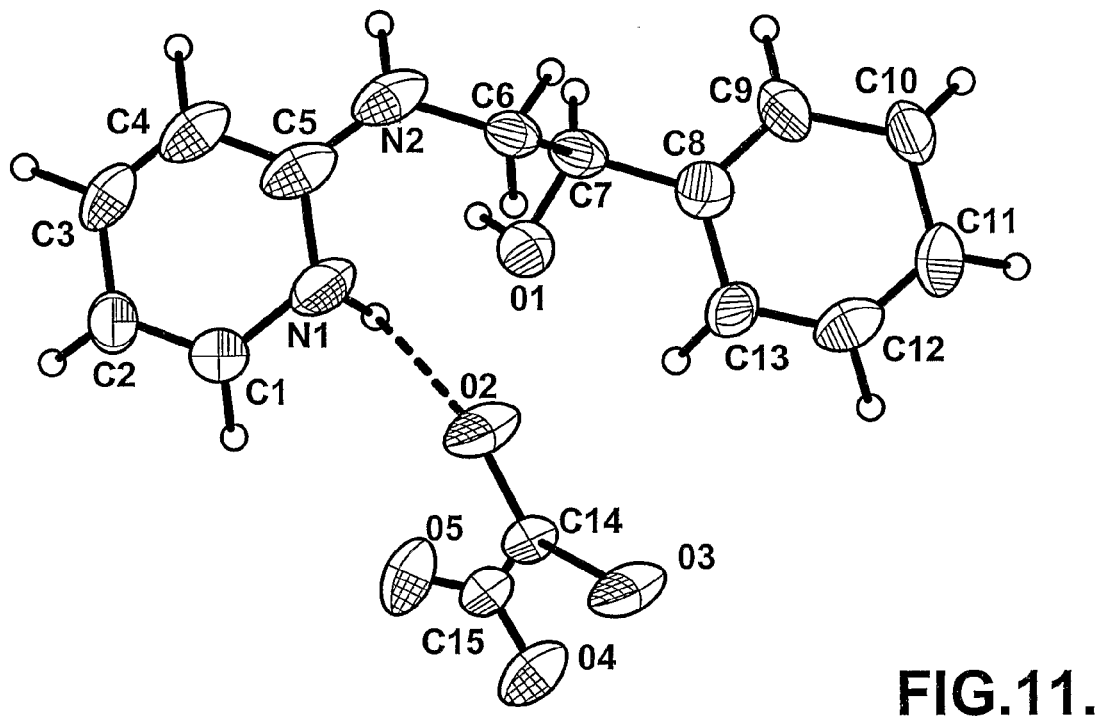
FIG. 11 indicates the crystal structure of the dextro isomer of phenyramidol oxalate.
Figure 12:
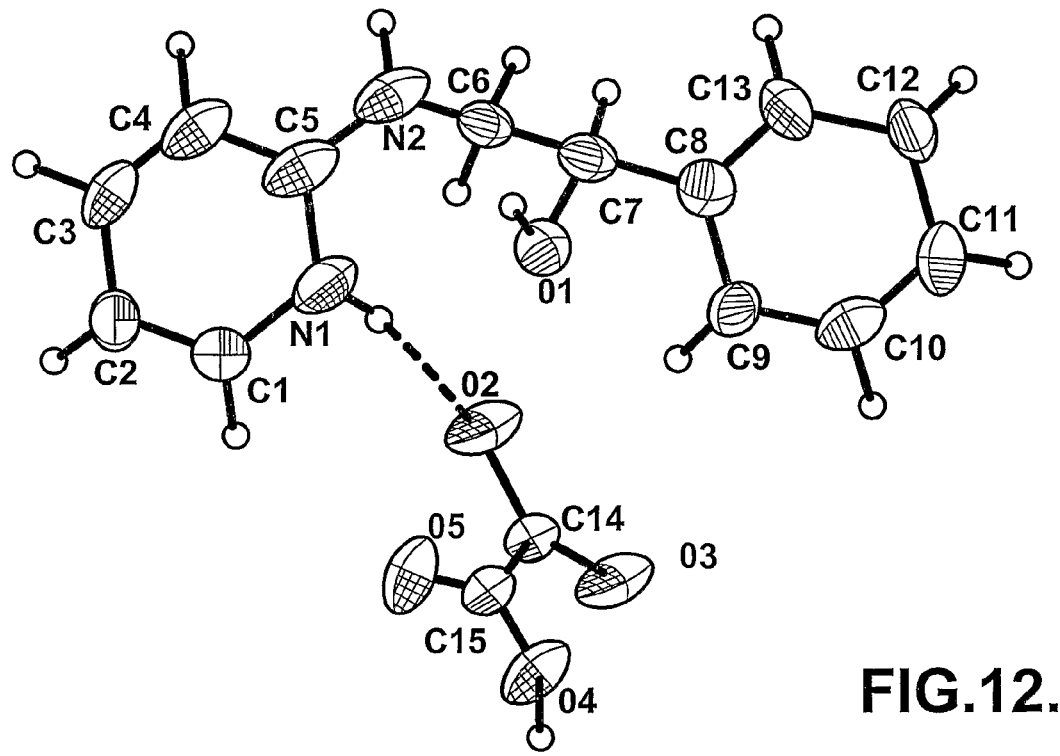
FIG. 12 indicates the crystal structure of the laevo isomer of phenyramidol oxalate.
Figure 13:
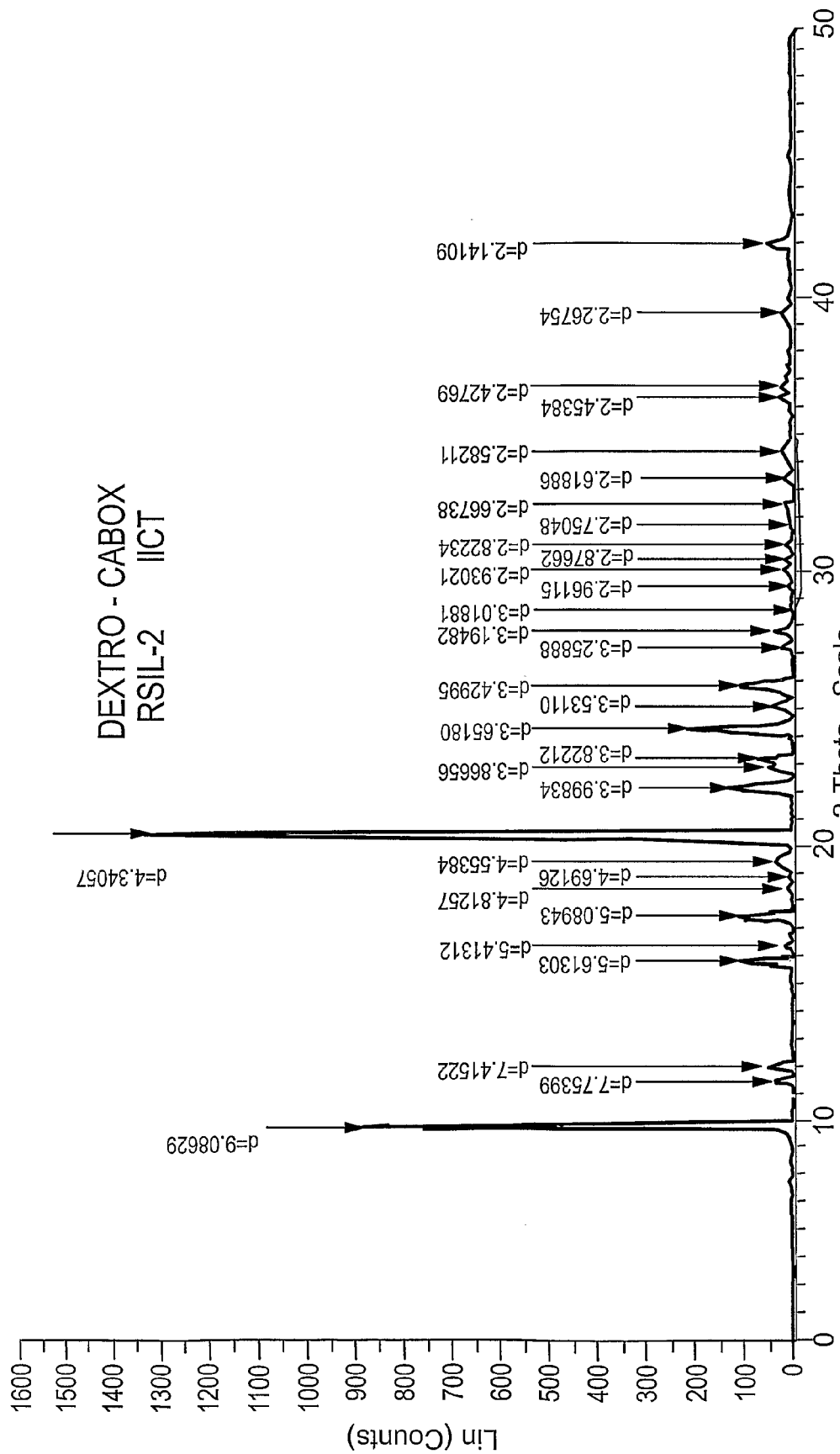
FIG. 13 depicts the X-ray crystallographic data of the dextro isomer of phenyramidol oxalate.
Figure 14:
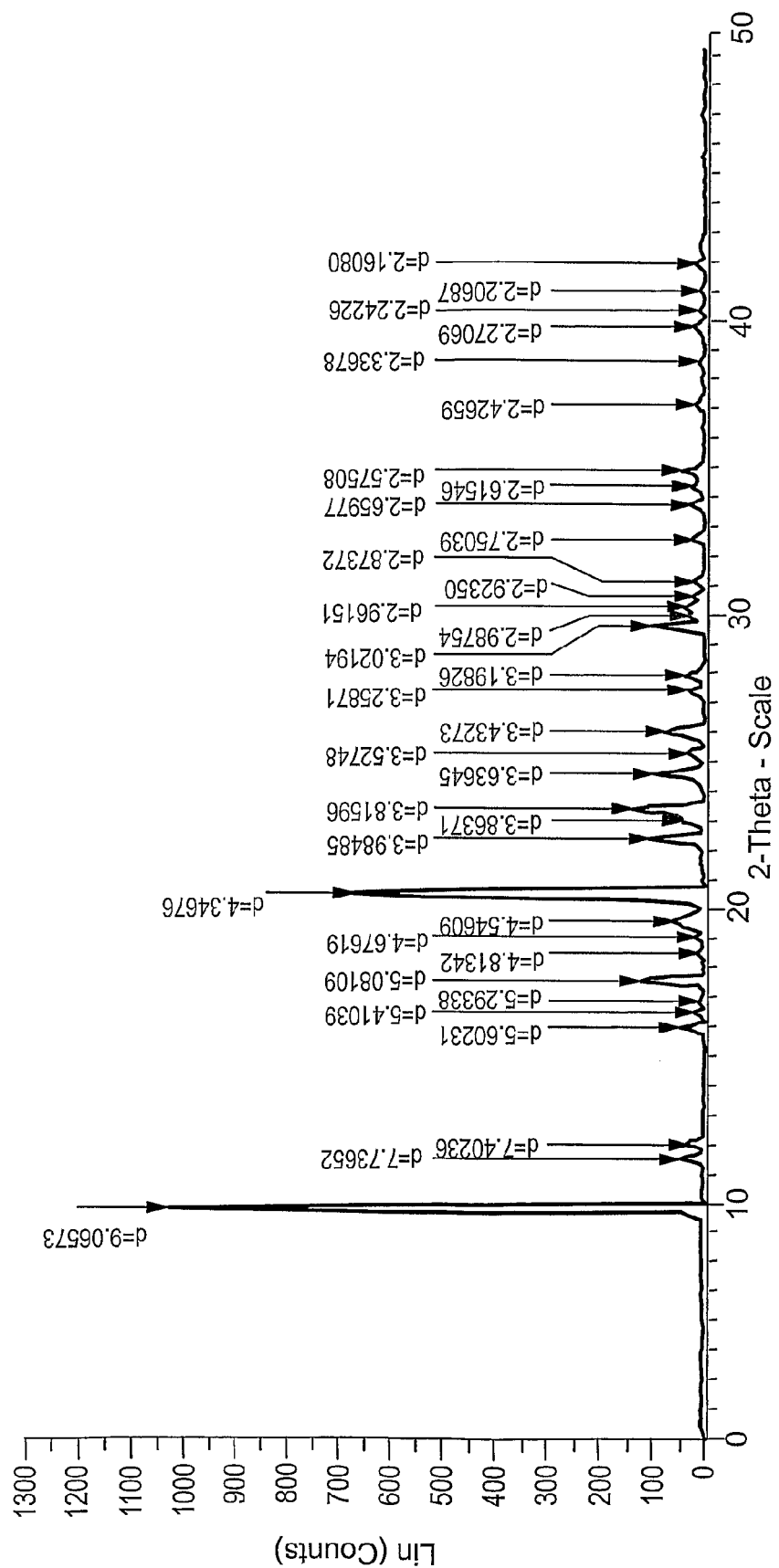
FIG. 14 depicts the X-Ray crystallographic data of the laevo isomer of phenyramidol oxalate.
Figure 15:
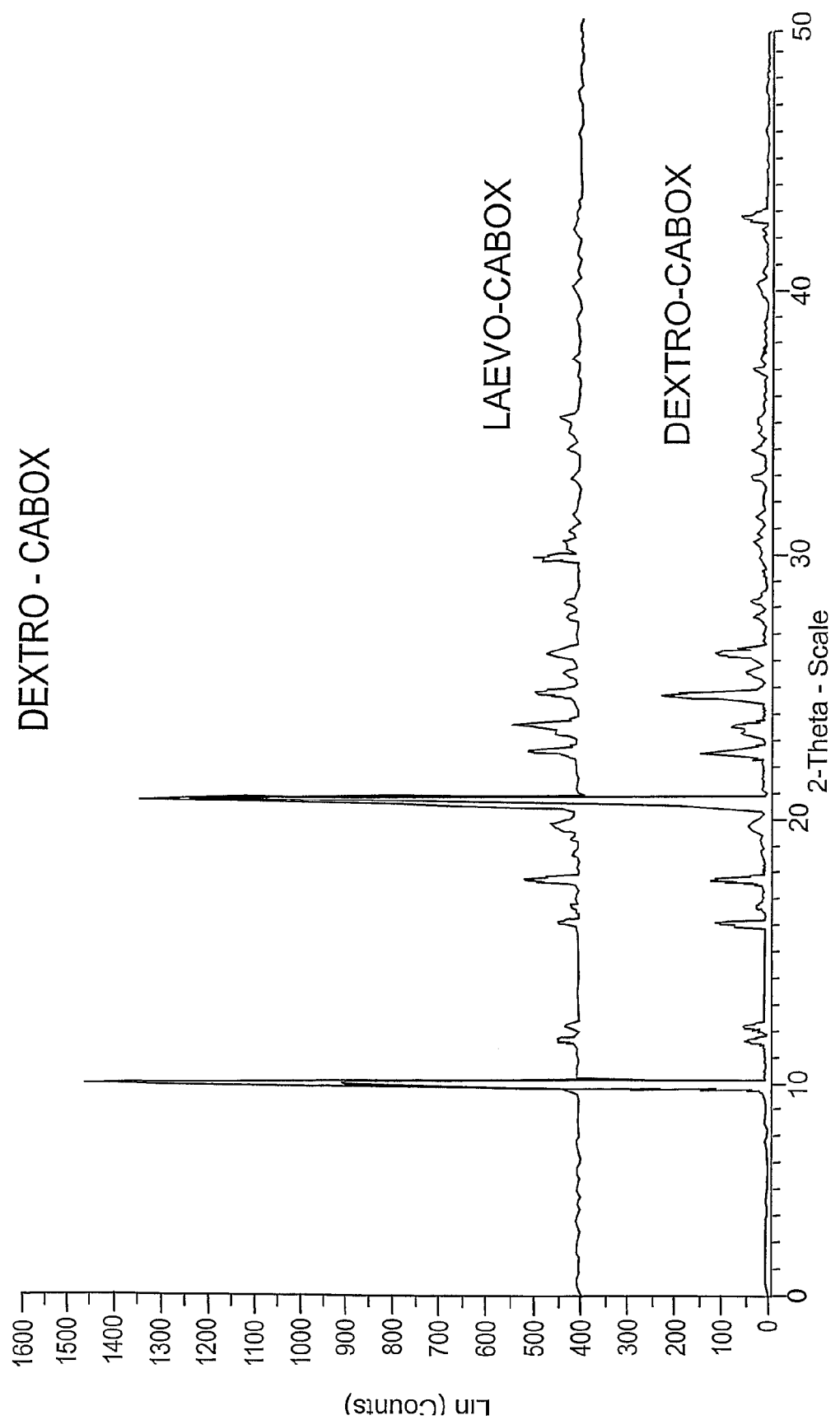
FIG. 15 depicts the superimposed X-Ray crystallographic data of dextro and laevo isomers of phenyramidol oxalate.
Figure 16:
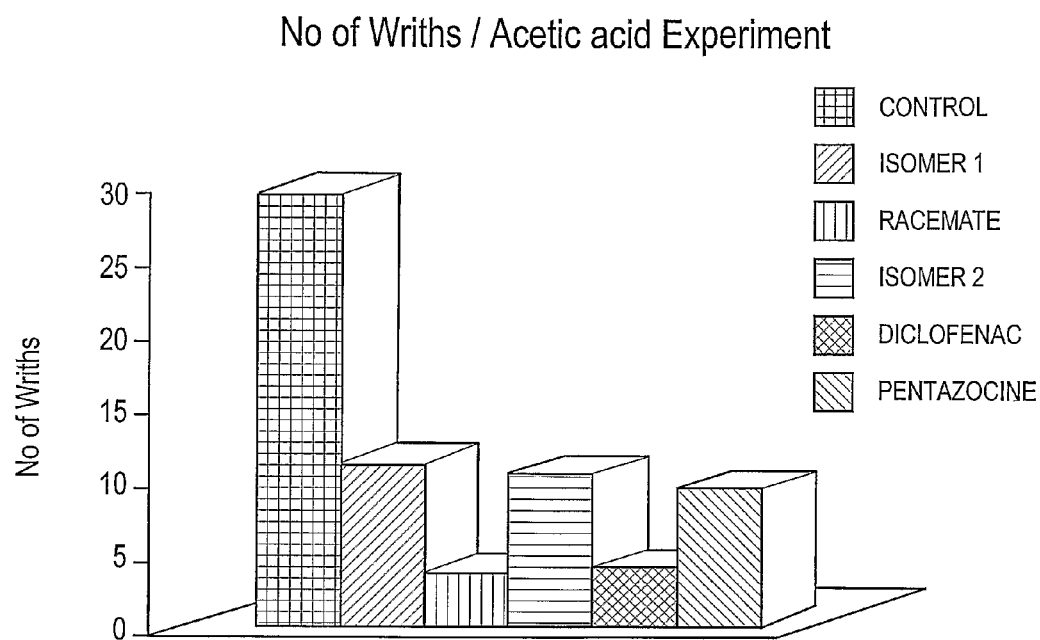
FIG. 16 shows the number of wriths by an acetic acid induced writhing method.
Figure 17:
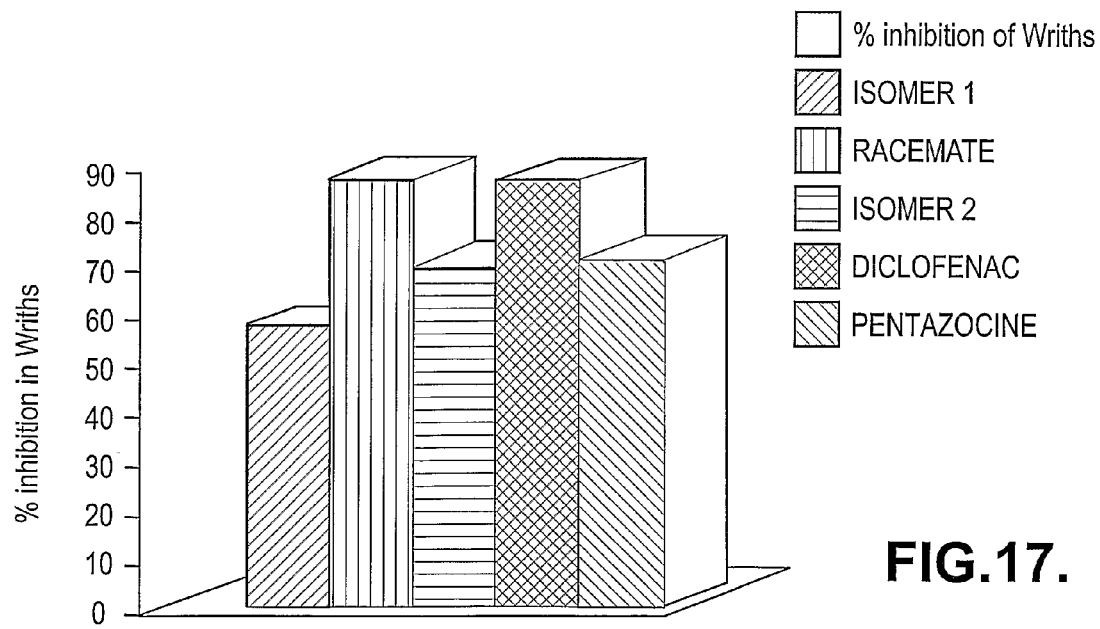
FIG. 17 shows the inhibition of the wriths after the administration of the tested formulations.

From the X-ray diffraction analysis, it is seen that both the enantiomers posses similar morphology, i.e., both the enantiomers posses orthorhombic structure with almost identical cell dimensions and volume. The X-Ray crystallographic data is shown in FIGS. 11 and 12.

The peaks of the X-ray single crystal analysis of the (R) laevo isomer are shown below.

| Angle 2-Theta ° | d value Angstrom | Intensity % % |
|---|---|---|
| 9.748 | 9.06573 | 100.0 |
| 11.428 | 7.73652 | 4.5 |
| 11.946 | 7.40236 | 3.3 |
| 15.806 | 5.60231 | 4.3 |
| 16.371 | 5.41039 | 2.1 |
| 16.735 | 5.29338 | 1.4 |
| 17.439 | 5.08109 | 11.8 |
| 18.421 | 4.81342 | 1.7 |
| 18.963 | 4.67619 | 1.9 |
| 19.511 | 4.54609 | 6.2 |
| 20.415 | 4.34676 | 65.8 |

TABLE 1

| | | Elemental analysis | | | | |
|---|---|---|---|---|---|---|
| | | % Actual | | | % Calculated (Theo.) | | |
| S. No. | Sample Name | Carbon | Hydrogen | Nitrogen | Carbon | Hydrogen | Nitrogen |
| 1 | (S)-Phenyramidol Oxalate | 59.376 | 5.72 | 9.396 | 59.21 | 5.26 | 9.21 |
| 2 | (R)-Phenyramidol Oxalate | 59.357 | 5.661 | 9.327 | | | |
| 3 | (S)-Phenyramidol Hydrochloride | 63.03 | 5.74 | 11.12 | 62.15 | 5.97 | 11.15 |
| 4 | (R)-Phenyramidol Hydrochloride | 63.04 | 5.66 | 11.15 | | | |

-continued

| Angle 2-Theta ° | d value Angstrom | Intensity % |
|---|---|---|
| 22.292 | 3.98485 | 10.7 |
| 23.000 | 3.86371 | 5.3 |
| 23.292 | 3.81596 | 13.9 |
| 24.459 | 3.63645 | 9.7 |
| 25.227 | 3.52748 | 3.6 |
| 25.935 | 3.43273 | 7.3 |
| 27.346 | 3.25871 | 3.2 |
| 27.873 | 3.19826 | 3.4 |
| 29.536 | 3.02194 | 10.1 |
| 29.884 | 2.98754 | 3.2 |
| 30.152 | 2.96151 | 4.0 |
| 30.554 | 2.92350 | 2.5 |
| 31.096 | 2.87372 | 2.0 |
| 32.529 | 2.75039 | 2.5 |
| 33.669 | 2.65977 | 2.8 |
| 34.257 | 2.61546 | 2.5 |
| 34.811 | 2.57508 | 4.5 |
| 37.017 | 2.42659 | 1.8 |
| 38.494 | 2.33678 | 1.2 |
| 39.661 | 2.27069 | 2.1 |

-continued

| Angle 2-Theta ° | d value Angstrom | Intensity % |
|---|---|---|
| 40.185 | 2.24226 | 1.1 |
| 40.858 | 2.20687 | 1.0 |
| 41.769 | 2.16080 | 2.1 |

The peaks of the X-ray single crystal analysis of the (S) dextro isomer are shown below.

| Angle 2-Theta ° | d value Angstrom | Intensity % |
|---|---|---|
| 9.726 | 9.08629 | 67.2 |
| 11.403 | 7.75399 | 3.3 |
| 11.925 | 7.41522 | 3.9 |
| 15.776 | 5.61303 | 8.4 |
| 16.362 | 5.41312 | 1.7 |
| 17.411 | 5.08943 | 9.0 |
| 18.421 | 4.81257 | 1.0 |
| 18.901 | 4.69126 | 1.1 |
| 19.477 | 4.55384 | 3.1 |
| 20.444 | 4.34057 | 100.0 |
| 22.216 | 3.99834 | 10.8 |
| 22.983 | 3.86656 | 4.0 |
| 23.254 | 3.82212 | 5.6 |
| 24.355 | 3.65180 | 16.9 |
| 25.200 | 3.53110 | 3.3 |
| 25.956 | 3.42995 | 8.5 |
| 27.345 | 3.25888 | 2.1 |
| 27.904 | 3.19482 | 2.7 |
| 29.567 | 3.01881 | 1.3 |
| 30.156 | 2.96115 | 2.2 |

-continued

| Angle 2-Theta ° | d value Angstrom | Intensity % |
|---|---|---|
| 30.482 | 2.93021 | 1.7 |
| 31.064 | 2.87662 | 1.8 |
| 31.677 | 2.82234 | 0.6 |
| 32.528 | 2.75048 | 2.6 |
| 33.570 | 2.66738 | 2.4 |
| 34.211 | 2.61886 | 1.5 |
| 34.714 | 2.58211 | 1.7 |
| 36.591 | 2.45384 | 2.5 |
| 36.999 | 2.42769 | 1.4 |
| 39.718 | 2.26754 | 2.0 |
| 42.172 | 2.14109 | 4.7 |

X-ray crystal structure studies indicate that dextro-isomer shows in 'sinister' or S-form and leavoisomer shows 'rectus' or R-form. The observations made from the crystallographic data are in conformity with the structure of the chiral substrate (styrene oxide). The specific optical rotation data is summarized in the following Table 1:

| | Styrene oxide | | Phenyramidol oxalate | | |
|---|---|---|---|---|---|
| S. No. | Configuration | Specific optical rotation | Configuration | Specific optical rotation | Remarks |
| 1 | R | +33° | R | −70.799° | Phenyramidol oxalate formed with styrene oxide configuration |
| 2 | S | −33° | S | +69.699° | Phenyramidol oxalate formed with styrene oxide configuration |

In another embodiment, the invention provides pharmaceutical compositions comprising substantially pure enantiomers of Phenyramidol or their salts useful in the treatment of management of pain and pain related disorders or symptoms. The term "substantially pure" means having purity equal to or greater than 99.9% and preferably a purity that is greater than 99.0%.

Substantially pure enantiomers of phenyramidol or their salts of the present invention can be formulated into variety of dosage forms along with commonly used inert excipients for administration to humans and mammals for pain management and related disorders or symptoms. When a dosage form such as a tablet is made by compaction of a powdered composition, the composition is subjected to pressure from a punch and dye. Solid and liquid compositions can also be dyed using any pharmaceutically acceptable colorant to improve their appearance and/or facilitate patient identification of the product and unit dosage level.

In liquid pharmaceutical compositions of the present invention, optical enantiomers of phenyramidol or pharmaceutically acceptable salts thereof and any other solid excipients are dissolved or suspended in a liquid carrier such as water, vegetable oil, alcohol, polyethylene glycol, propylene glycol or glycerin. Liquid pharmaceutical compositions can contain emulsifying agents to disperse uniformly throughout the composition an active ingredient or other excipient that is not soluble in the liquid carrier.

Selection of particular excipients and the amounts to use can be readily determined by the formulation scientist based upon experience and consideration of standard procedures and reference works in the field. The solid compositions of the present invention include powders, granulates, aggregates and compacted compositions.

Selection of excipients in the preparation of injectable formulations and the amounts to use can be readily determined by a formulation scientist based on the standard procedures in the pertinent field.

Yet in another embodiment, the invention describes clinical evaluation of (R) and (S) enantiomers of Phenyramidol hydrochloride for enhanced/newer therapeutic benefits. The study design of clinical evaluation of R and S enantiomers of Phenyramidol hydrochloride for enhanced therapeutic benefits described herein below.

Further, the present invention comprises the studies which include the evaluation of skeletal muscle relaxant activity, analgesic activity and pharmacological activity of the racemic, (R) and (S) isomers or their salts and therapeutic dosage forms containing the same. The benefits of the present invention extend to the following:

1. Equipotent therapeutic results with lesser dosage schedule;
2. Lesser side effects because of equipotent therapeutic action in lesser dosage;
3. Better safety margin as muscle relaxant and hence becomes a preferred injectable in pre/post management of surgical patients. (in Gynecology, Cardiac, Orthopedic, CNS, Dental as well as general surgeries);
4. Sustained release preparation with chiral molecules is achievable with lesser dosage as compared to 1200 or even to 800/600 mgs of conventional Phenyramidol, thereby providing a superior option with better patient compliance to racemic Phenyramidol;
5. Compositions containing (S)/(R) isomer are more potent (i.e. equipotent in smaller doses) when compared with formulations containing racemic Phenyramidol as an active ingredient;
6. Compositions containing (S)/(R) isomers cause lesser side effects as compared to formulations containing racemic Phenyramidol as an active ingredient;
7. Compositions containing (S)/(R) isomer offers better therapeutic and safety ratio as compared to conventional Phenyramidol; and
8. Compositions containing (S)/(R) isomer may offer additional therapeutic advantages in allied and other indications (e.g. fever and inflammation).

The following examples, which include preferred embodiments, will serve to illustrate the practice of this invention, being understood that the particulars shown are by way of example and for purpose of illustrative discussion of preferred embodiments of the invention, and are not limiting the scope of the invention.

Example 1

Process for Synthesis of (R)-Phenyramidol

In a dry reaction flask, 0.18 mole of lithium amide was taken in dimethylformamide (75 ml), added to a solution of 0.165 mole of 2-aminopyridine dissolved in dimethylformamide (30 ml) at 10-30° C. under stirring and the stirring was further continued for 30-60 minutes at the same temperature. The reaction mixture was heated at a temperature of 80° C. and the generated ammonia gas was removed by applying the vacuum. 0.18 moles of (R)-styreneoxide was added 10 drop wise to the reaction mass at a temperature of 90° C. in 1 hr and the reaction mass was maintained at the same temperature for 20-40 mins. The reaction mass was heated up to 110° C. till the completion of reaction and maintained for 20 mins at the same temperature. The solvent dimethylformamide was distilled under reduced pressure. A mixture of Toluene (75 ml) and DM water (150 ml) was added to the reaction mass and stirred at 65° C. for 10-20 min. The organic layer was separated, dried over anhydrous sodium sulphate and evaporated under vacuum to obtain brown coloured viscous liquid.

Specific Rotation: [a]=−40.29 (c=1, methanol)

Yield of the crude base: 40 gm (R) Phenyramidol free base 137 gm (0.64 mole) was taken in methanol (400 ml) and refluxed with activated charcoal (10 gm) for 0.5 to 1.0 h, and filtered the hot solution over celite bed and washed with methanol (75 ml) and the filtrate was concentrated to get the free base.

Example 2

Process for Synthesis of (R)-Phenyramidol Oxalate Salt 0.64 moles of (R) Phenyramidol free base (137 gm) was taken in ethyl acetate (400 ml) and heated up to 70° C. Separately oxalic acid dihydrate 80 gm (0.63 mol) was dissolved under heating in ethyl acetate (300 ml) and added to phenyramidol solution. The reaction mass was cooled to room temperature under stifling. The solid separated was filtered and washed with hot ethyl acetate (150 ml) and suck dried under vacuum.

Specific rotation: [a]=−59.099° (c=1, methanol)

Yield: 180 gms (crude salt)

M.P: 145-154° C.

To further purify, the oxalate salt (261 gm) was dissolved in methanol (1.75 L) and refluxed with activated charcoal (25 gm) for 0.5-10 h, filtered the hot solution over celite bed and washed with methanol (150 ml). The filtrate was concentrated approximately to 1 L and cooled to room temperature with stirring. The solid separated was filtered under reduced pressure and washed with ethyl acetate and suck dried under vacuum.

Specific rotation: [a]=−70.799° (c=1, methanol)

Specific rotation: [d]=−32.499° (c=1, water)

Melting point: 163-165° C.

Yield: 76%

HPLC Purity: 99.5%

Chiral Purity: 99% e.e

NMR(CDCl3) d: 3.27 (t, 11-1), 3.52 (m, 1H) 4.75 (dd, 1H), 6.56 (t, 1H), 6.95 (d, 1H), 7.37 (m, 6H), 7.94 (d, 1H)

Example 3

Process for Synthesis of (R)-Phenyramidol Hydrochloride Salt 0.296 moles of (R)-Phenyramidol Oxalate (90 gms) was dissolved in 1.3 liters of de-mineralized water and stirred at 50° C. The pH of the clear solution was between 4 to 5, which was cooled to 20° C. and made alkaline (pH>8) by adding 55 gms of sodium bicarbonate. Precipitated solid was stirred at 28-30° C. for 1 hour, filtered and washed with (500 ml) water and dried under vacuum at 40° C. for 3 hours. Phenyramidol base (61 gms) was dissolved in 180 ml of methanol and refluxed for 1 hour with 6 gms of activated charcoal, filtered, washed with 50 ml of methanol and the filtrate was evaporated to get colourless solid.

Specific rotation: [a]=−38.76° (c=1, methanol)
Yield: 60 gms
M.P: 105-110° C.
HPLC Purity: >99%
Chiral Purity: 99% e.e.

0.420 moles of (R)-Phenyamidol free base (90 gm) was dissolved in ethanolic hydrochloride (14-16%) under stifling at 28-30° C. The clear solution was cooled to 0-5° C. under stirring for 2-3 hours and after 1 hour solid precipitated out. The reaction mass was stirred further at 0 to −5° C. overnight, filtered, washed with 25 ml of chilled ethanol. The colourless solid, (R) Phenyramidol hydrochloride obtained was dried at 45-50° C. under vacuum.

Specific rotation: [a]=−104.59 (c=1, Methanol)
Melting point: 125-128° C.
Yield: 51 gm
HPLC Purity: >99%
Chiral Purity: 99% e.e
NMR(CDCl$_3$) δ: 3.41-3.69 (m, 2H), 4.84 (dd, 11-1), 5.81 (br, 1H) 6.79 (t, 1H), 7.16 (d, 1H), 7.30 (m, 3H), 7.49 (d, 2H), 7.84 (t, 2H), 9.10 (br, 1H) and 13.96 (br, 1H)

Example 4

Process for Synthesis of (S)-Phenyramidol 0.165 mole of 2-aminopyridine (15.56 gm) dissolved in dimethylformamide (30 ml) was added slowly to the suspension of 0.18 moles of lithium amide (4.08 gm) in dimethylformamide (75 ml), at 10-30° C. under stirring and the stirring was further continued for 30-60 minutes at the same temperature, The temperature of the reaction mixture was raised up to 80° C. and vacuum was applied to remove the generated ammonia. 0.18 moles of (S)-styreneoxide (22 gm) was added drop wise to the reaction mass at 90° C. up to 1 hr and the reaction mass was maintained at the same temperature for 20-40 mins. The temperature of the reaction mass was further raised to 100° C. and maintained for 20 mins at the same temperature. The temperature was reduced 60° C. and dimethylformamide was distilled under 5 reduced pressure. A mixture of Toluene (75 ml) and DM water (150 ml) was added to the reaction mass and stirred at 60° C. for 10-20 min. The organic layer was separated, dried over anhydrous sodium sulphate and evaporated under vacuum to obtain brown coloured viscous liquid.

Specific Rotation: [a]=+38.899 (c=1, methanol)
Yield of the crude base: 106 gm 240 gm of (S) Phenyramidol free base (1.12 mole) was taken in methanol (400 ml) and refluxed with activated charcoal (10 gm) for 0.5 to 1.0 h, and filtered the hot solution over celite bed and washed with methanol (75 ml) and the filtrate was concentrated to get the free base (137 gm).

Example 5

Process for Synthesis of (S)-Phenyramidol Oxalate (S) Phenyramidol free base (137 gm) was taken in ethyl acetate (400 ml) and heated up to 65° C. Separately, 140 gm of oxalic acid dihydrate (1.11 mol) was dissolved in ethyl acetate (350 ml) under heating and added to phenyramidol solution. The reaction mass was cooled to room temperature under stirring. The solid separated was filtered and washed with hot ethyl acetate (150 ml) and suck dried under vacuum.

Specific rotation: [a]=+54.899° (c=1, methanol
M.P: 145-154° C.
Yield of the crude oxalate: 319 gm To further purify, the crude (S) oxalate salt (315 gm) was dissolved in methanol (2 L) and refluxed with activated charcoal (25 gm) for 1 h, filtered the hot solution over celite bed and washed with methanol (400 ml). The filtrate was concentrated approximately to 1 L and cooled to room temperature with stirring. The solid separated was filtered under reduced pressure, washed with ethyl acetate (300 ml) and suck dried under vacuum.

Specific rotation: [a]=+69.699° (c=1, methanol)
Specific rotation: [a]=+31.499° (c=1, water)
Melting point: 163-165° C.
Yield: 148 gm
HPLC Purity: 99.5%
Chiral Purity: 99% e.e
NMR(CDCl$_3$) δ: 3.27 (t, 1H), 3.52 (m, 1H) 4.75 (dd, 1H), 6.56 (t, 1H), 6.95 (d, 1H), 7.37 (m, 6H), 7.94 (d, 11-1).

Example 6

Process for Synthesis of (S)-Phenyramidol Hydrochloride Salt 0.296 moles of (S)-Phenyramidol Oxalate (90 gms) was dissolved in 1.3 liters of de-mineralized water and stirred at 500 C. The pH of the clear solution is 4-5, which was cooled to 20° C. and made alkaline (pH>8) by adding 55 gms of sodium bicarbonate. Precipitated solid was stirred at 28-30° C. for 1 hour, filtered and washed with (500 ml) water and dried under vacuum at 40° C. for 3 hours. Phenyramidol base (61 gms) was dissolved in 180 ml of methanol and refluxed for 1 hour with 6 gms of activated charcoal, filtered, washed with 50 ml of methanol and the filtrate was evaporated to get colourless solid.

Specific rotation: [a]=+38.878° (c=1, methanol)
Yield: 60 gms
M.P: 109-110° C.
HPLC Purity: >99%
Chiral Purity: 99% e.e.

0.420 moles of (S)-Phenyramidol free base (90 gm) was dissolved in ethanolic hydrochloride (14-16%) under stirring at 28-30° C. The clear solution was cooled to 0-5° C. under stirring for 2-3 hours and after 1 hour solid precipitated out. The reaction mass was stirred further at 0 to −5° C. overnight, filtered, washed with 25 ml of chilled ethanol. The colourless solid, (S) Phenyramidol hydrochloride obtained was dried at 45-50° C. under vacuum.

Specific rotation: [a]=+104.0 (c=1, Methanol)
Melting point: 125-128° C.
Yield: 50 gm
HPLC Purity: >99%
Chiral Purity: 99% e.e
NMR(CDCl$_3$) d: 3.49-3.68 (m, 2H), 4.84 (dd, 1H), 5.81 (br, 1H) 6.80 (t, 1H), 7.16 (d, 1H), 7.26 (m, 3H), 7.49 (d, 2H), 7.84 (t, 2H), 9.10 (br, 1H) and 14.0 (br, 1H)

Example 7

Skeletal Muscle Relaxant Activity of the Test Formulations in Mice

The evaluation of skeletal muscle relaxant activity of the formulations containing phenyramidol racemic, dextro and laevo isomers of oxalate salts in swiss albino mice were carried out using Rota rod apparatus. Each animal was trained only once per day for 5 days. Mice demonstrating the ability to remain on the rod rotating at 25 rpm for at least 60 seconds were included in the test. Mouse was placed on rota rod only when it achieved the speed of 25 rpm. The 'fall off time' in seconds was noted down when the mouse falls from rotating rod. Endurance time was measured up to 120 seconds. The skeletal muscle relaxant activity was assessed using 0 hr, 1 hr, 2 hrs, 4 hrs and 6 hrs time points after the dose administration. A total of 100 mice were selected and randomly distributed into ten main groups with 10 animals per group.

Control group receiving only vehicle served as a placebo in the study. Treatment group consisted of Compound A (T3), Compound B (T1, T1 H, TI M, T1 L) and Compound C (T2, T2H, T2M, T2L). Compound T3 had only one dose 2400 mg, hence the number of mice were only 10 for the total treatment. However, Compound B (T1) and Compound C (T2) had 4 doses 1200 mg, 1600 mg, 2000 mg and 2400 mg as mentioned above, hence had 40 mice each in their respective groups.

Human daily dose of 2400 mg was extrapolated to mice for compound T3 and human daily dose of 1200 mg, 1600 mg, 2000 mg and 2400 mg was extrapolated to mice for compound T1 and T2. The test formulations were administered by oral route through gavage tube.(p.o.).

The groups were as follows: Each group consisted of 10 mice and the dosage of the test formulations administered was as follows (Table 2)

TABLE 2

| Sr. No. | Treatment Code | Drug Name | Name of the drug |
|---|---|---|---|
| 1 | T1 | Phen-2 (2400 mg) | Phenyramidol oxalate (+) |
| 2 | T1H | Phen-2 (2000 mg) | Phenyramidol oxalate (+) |
| 3 | T1M | Phen-2 (1600 mg) | Phenyramidol oxalate (+) |
| 4 | T1L | Phen-2 (1200 mg) | Phenyramidol oxalate (+) |
| 5 | T2 | Phen-4 (2400 mg) | Phenyramidol oxalate (−) |
| 6 | T2H | Phen-4 (2000 mg) | Phenyramidol oxalate (−) |
| 7 | T2M | Phen-4 (1600 mg) | Phenyramidol oxalate (−) |
| 8 | T2L | Phen-4 (1200 mg) | Phenyramidol oxalate (−) |
| 9 | T3 | Phen-3 2400 mg | Phenyramidol Racemate |
| 10 | R1 | Control (5% Gum acacia) | Placebo (Gum acacia) |

Note:
Human dosages are extrapolated for animal experiments.

Two efficacy variables were assessed during the experiment: 1. Percent animal falling from the rod was noted; 2. Endurance Time (ET): The time taken for a mouse to fall from the rod was taken as endurance time. The endurance time was taken up to 120 sec and treatment group ET was compared to normal control. These efficacy variables were assessed at five time points 0 hr, 1 hr, 2 hr, 4 hr, and 6 hr for each and every animal.

The data from the Rota-rod test as described above in Table 2 exhibits that Compound T3 at 2400 mg showed significant difference ($p<0.01$) from normal control in endurance time at 1 hr, 2 hr and 4 hr time interval after drug administration. Compound T1 showed significant difference ($p<0.05$) from normal control at doses 1600 mg, 2000 mg and 2400 mg at 1 hour time interval. Compound T2, however showed significant difference ($p<0.05$) from normal control only at dose 2400 mg at 1 hour time interval. The results indicate that the test formulations (TI, T2 and T3) exhibit skeletal muscle relaxant activity at the doses mentioned above.

In another experiment, the studies have been extended to confirm the isomer which is having more skeletal muscle relaxant activity. Control group (R1) receiving only vehicle (water for injection) served as a placebo in the study. Treatment group consisted of Compound T1 (racemic molecule), Compound T2 (S isomer) and Compound T3 (R isomer). Human daily dose of 2400 mg was extrapolated to mice for compound T1; T2 and T3.

Statistical Methods:

Statistical analysis of the parameters and comparisons between dose groups was performed using One-Way ANOVA. A p-value<0.05 in the one-way ANOVA indicates a statistically significant difference among any pair of dose groups. To find out which pair of dose groups differed significantly, the Dunnett's multiple comparison test was used. A $p<0.05$ in the Dunnett's test indicate significant difference between the pair of dose groups being tested. The results are discussed in Table 3.

TABLE 3

| % Animals falling off the Rota rod in 120 sec at | | | | | |
|---|---|---|---|---|---|
| Groups | 0 hr | 30 mins | 60 mins | 1.5 hr | 2 hr |
| R1 | 0 | 10 | 10 | 0 | 0 |
| (T1) | 0 | 100 | 40 | 50 | 30 |
| (T2) | 0 | 100 | 77.77 | 77.77 | 88.88 |
| (T3) | 0 | 100 | 80 | 50 | 10 |

| Groups | 0 hr | 30 mins | 60 mins | 1.5 hr | 2 hr |
|---|---|---|---|---|---|
| R1 | 120 ± 0 | 118.1 ± 6.00 | 119.7 ± 0.94 | 120 ± 0.0 | 120 ± 0.0 |
| (T1) | 120 ± 0 | 0 ± 0** | 88.6 ± 43.81 | 100.7 ± 24.27 | 98.5 ± 37.42 |
| (T2) | 120 ± 0 | 0 ± 0** | 67.44 ± 33.63** | 83 ± 27.31** | 87.44 ± 27.36* |
| (T3) | 120 ± 0 | 0 ± 0** | 73.20 ± 37.74* | 111.3 ± 9.90 | 118.6 ± 3.09 |

Note:
(Ti) Phenyramidol racemate - 2400 mg; (T2)Phenyramidol HCI (+) - 2400 mg and (T3) Phenyramidol HCI (−) - 2400 mg. Values are expressed as mean ± SD. (n = 10) Significantly different from vehicle control group *($p<0.05$) and **($p<0.01$) after application of One way ANNOVA followed by Dunnett's test for statistical significance.

The data from the rota-rod test exhibited that Compound T1, T2 and T3 at 2400 mg showed significant difference (p<0.01) from normal control in endurance time at 0.5 hr interval after drug administration. Compound T1 showed no significant difference (p>0.05) from normal control at 1, 1.5, and 2 hr time interval. Compound T2, however showed significant difference (p<0.01) from normal control at 1, 1.5, and (p<0.05) at 2 hr time interval. Compound T3 showed significant difference (p<0.05) at only 1 hr interval, followed by no significant difference (p>0.05) from normal control at 1.5 and 2 hr interval.

The results indicate that the test formulations (Compound T1, T2 and T3) exhibit skeletal muscle relaxant activity at the time points mentioned above. From the above, it is concluded that compound T2 possess excellent skeletal muscle relaxant activity.

Example 8

Analgesic Activity of the Tested Formulations in Mice

The objective of the study was to evaluate the analgesic activity of the tested formulations of the compounds of the present invention. The test was conducted in Swiss albino mice using acetic acid induced writhing method. A total of 78 pre-screened mice (showing writhing response within 10 minutes*) were divided into 6 groups of 13 animals (6 males+7 females) each. The animals showing no writhing response within 10 mins were excluded. Diclofenac and pentazocine were used as positive controls. The formulations were given orally to the different groups of animals and the number of writhes counted for a period of 15 minutes, after the onset of writhes. If the onset of writhes occurred 30 after 10 minutes the number of writhes was recorded as V. The time of onset of writhes was recorded for each animal.

The control group received 1% gum acacia. The Groups 2, 3, and 4 received the formulations viz: Phen 2; Phen 3 and Phen 4 respectively. Diclofenac and pentazocine were used as positive control and given to groups 5 and 6 respectively. Diclofenac, a potent analgesic & anti-inflammatory agent; and 5 pentazocine an opoid analgesic were selected for comparative evaluation of test formulations. Both these drugs were administered to different groups of animals at the dose of 2 mg/kg. The group 1 (Phen 1) served as—Ve Control group in the study. Phen 5 (Diclofenac—2 mg/kg) and Positive Control: Phen 6 (Pentazocine 2 mg/kg) served as positive controls.

Human daily dose of 2400 mg (800 mg×3 times) was extrapolated to mice for Phen3 and human daily dose of 1200 mg (400 mg×3 times) was extrapolated to mice for Phen2 and Phen 4. The numbers of writhes observed are given below in Table 4 for each formulation.

The results shown in Table 4 below indicate that the test formulation (Phen 2, Phen 3 and Phen 4) showed significant analgesic activity by decrease in the number of writhes induced by acetic acid. The positive control also exhibited significant analgesic activity.

TABLE 4

| Groups | Name of the drug | Average no. of writhes |
| --- | --- | --- |
| Phen 1 | Placebo (Gum Acasia) | 29.62 ± 6.87 |
| Phen 2 | Phenyramidol oxalate (+) | 13.08 ± 9.93* |
| Phen 3 | Phenyramidol Racemate | 3.54 ± 3.95* |
| Phen 4 | Phenyramidol oxalate (−) | 12.08 ± 4.21* |
| Phen 5 | Positive Control (Diclofenac) | 4.08 ± 6.32* |
| Phen 6 | Positive Control (Pentazocine) | 10.62 ± 9.47* |

Further, the evaluation of analgesic activity was carried out using variable dosage forms with different groups. A total of 100 animals (50 males+50 females) were selected randomly and distributed into ten main groups with 10 animals per group (5 M+5 F). Human daily dose of 2400 mg (800 mg×3 times) was extrapolated to mice for Phen 3 (Phenyramidol Racemic (Hydrochloride) and human daily dose of 1200 mg (400 mg×3 times), 1800 mg (400 mg×4.5 times), 2000 mg (400 mg×5 times) & 2400 mg (400 mg×6 times) was extrapolated to mice for Phen2 and Phen4 groups.

The control group 1 received 1% gum acacia and served as negative control group. Groups 2, 3, 4 & 5 received the formulation Phen2. Groups 6, 7, 8 & 9 received the formulation Phen 4 (Isomer 2) & Group 10 received the formulation Phen 3 (Racemic). The results are shown below in Table 5.

TABLE 5

| Groups | Dose | Name of the drug | Average no. of writhes |
| --- | --- | --- | --- |
| 1) Phen 1 (Gum acacia) | 1% Soln. | Placebo (Gum Acasia) | 30.80 ± 4.44 |
| 2) Phen 2 (Isomer 1) | 1200 mg | Phenyramidol oxalate (+) | 11.90 ± 8.43* |
| 3) Phen 2 (Isomer 1) | 1800 mg | Phenyramidol oxalate (+) | 8.80 ± 6.78* |
| 4) Phen 2 (Isomer 1) | 2000 mg | Phenyramidol oxalate (+) | 8.20 ± 7.30* |
| 5) Phen 2 (Isomer 1) | 2400 mg | Phenyramidol oxalate (+) | 6.00 ± 5.66* |
| 6) Phen 4 (Isomer 2) | 1200 mg | Phenyramidol oxalate (−) | 10.50 ± 6.65* |
| 7) Phen 4 (Isomer 2) | 1800 mg | Phenyramidol oxalate (−) | 6.20 ± 5.39* |
| 8) Phen 4 (Isomer 2) | 2000 mg | Phenyramidol oxalate (−) | 6.00 ± 6.41* |
| 9) Phen 4 (Isomer 2) | 2400 mg | Phenyramidol oxalate (−) | 4.50 ± 5.19* |
| 10) Phen 3 (Racemic) | 2400 mg | Phenyramidol racemate | 4.20 ± 3.77* |

Values are expressed as mean ± SD. (n = 10).
*Significantly different from vehicle control group (p < 0.05).

The results indicate that the test formulation Phen 2, Phen 3 and Phen 4 showed significant analgesic activity by decrease in the number of writhes induced by acetic acid. Test formulations showed significant analgesic activity in acetic acid induced writhing model.

Further, one more experiment was done with phenyramidol hydrochloride to evaluate the analgesic activity at lesser dosage levels using acetic acid induced method. A total of 50 animals (25 males+25 females) were selected and randomly distributed into five main groups with 10 animals per group (5 M+5 F). 5 Human daily dose of 600 mg (400×1.5 times) & 1200 mg (800 mg×1.5 times) was extrapolated to mice for Phen 3 (Racemic) and human daily dose of 600 mg (400 mg×1.5 times) was extrapolated to mice for (−) Phenyramidol Hydrochloride & (+) Phenyramidol Hydrochloride and the results are discussed in Table 6.

TABLE 6

| Groups | Dose | Average no. of writhes |
| --- | --- | --- |
| 1) −Ve Control (Distilled water) | — | 29.50 ± 6.65 |
| 2) (−) Phenyramidol Hydrochloride | 600 mg | 3.20 ± 4.16* |
| 3) (+) Phenyramidol Hydrochloride | 600 mg | 5.00 ± 4.64* |
| 4) Phen 3 (Phenyramidol Racemic) | 600 mg | 5.90 ± 6.14* |
| 5) Phen 3 (Phenyramidol Racemic) | 1200 mg | 1.50 ± 2.59* |

Values are expressed as mean ± SD. (n = 10).

The results indicated as above that the test formulations with lesser amounts of dosage forms containing (S) Phenyramidol Hydrochloride, Phen 3 (Racemic) and (R) Phenyramidol Hydrochloride showed significant analgesic activity by decrease in the number of writhes induced by acetic acid.

In another experiment, analgesic activity of the Phenyramidol and its isomers has been carried out in mice by tail flick analgesiometer. Tail flick method was used for the evaluation of central analgesic activity. The test is very useful for discriminating between centrally acting morphine-like analgesics and non-opiate analgesics.

The tail flick latency was assessed by the tail flick analgesiometer (SECOR India. Delhi). The strength of current passing through naked nicrome wire was kept constant at 5 Amps. The basal reaction time was noted by placing the tip (last 1-2 cm) of the tail near the heat source.

The distance between heat source and the tail skin was 1 cm. The tail withdrawal from the heat source (flicking response) was taken as an end point. The cut-off reaction time was fixed at 10-12 seconds to avoid tissue damage. Human daily dose of 2400 mg (800 mg×3 time) was extrapolated to mice for compound TI and human daily dose of 1200 mg (400×3 times) was extrapolated to mice for compound T2 and T3. R2 and R3 are taken as control formulations. R1 is taken as negative control. The results were shown below in Table 7.

TABLE 7

| Name of the drug | Groups | Tail Flick Reaction Time (Sec.) | |
| --- | --- | --- | --- |
| | | 1 hr. | 4 hr. |
| Phenyramidol oxalate (+) | Phen 2 (T1) | 4.31 ± 1.754 | 2.46 ± 0.591 |
| Phenyramidol oxalate (−) | Phen 4 (T2) | 2.87 ± 1.071 | 3.18 ± 1.540 |
| Phenyramidol Racemate | Phen 3 (T3) | 4.86 ± 3.023 | 5.055 ± 2.735* |
| Placebo (Gum Acasia) | Phen 1 (R1) | 4.06 ± 1.224 | 3.11 ± 1.070 |
| Positive Control | Diclofenac (R2) | 3.41 ± 1.421 | 2.48 ± 0.654 |
| Positive Control | Pentazocin (R3) | 3.0 ± 0.7055 | 3.0 ± 0.7055 |

Test formulation Phen3 showed significant analgesic activity at 4 hr. Animals treated with test formulation Phen3, showed increase in tail flick latency as compared to control at the end of 4 hrs after dose administration, indicates the centrally mediated analgesic activity of test formulation Phen3. Other test compounds failed to exhibit any analgesic response. The observed central analgesic activity of the isomer of phenyramidol hydrochloride appears significantly important in view of the fact that peripheral analgesics amount to more than 95% of the analgesic market share.

Example 9

Anti-Arthritic Activity of the Formulations in Mice Containing Phenyramidol Oxalates The anti-arthritic activity was assessed using following time points after the injection of formalin 2 hrs, 4 hrs, 8 hrs, 24 hrs, 48 hrs and 72 hrs. The control group (group 1) received 1% gum acacia. The Groups 2, 3, and 4 received the formulations viz: Phen 2, Phen 3 and Phen 4 respectively. Diclofenac was used as positive control and given to group 5. Human daily dose of 2400 mg (800 mg×3 times) was extrapolated to rats for 5 (racemate) Phen 3 and human daily dose of 1200 mg (400 mg×3 times) was extrapolated to rats for (isomer 1) Phen 2 and (isomer 2) Phen 4. Diclofenac sodium 2 mg/Kg was used as reference product.

Initial or 0 hr thickness of the joint of right paw of each animal was recorded. The thickness of the joint was measured using Vernier calipers at different time intervals after the injection of formalin. These efficacy variables were assessed at six time points 2 hrs, 4 hrs, 8 hrs, 24 hrs, 48 hrs and 72 hrs for each and every animal. The results are presented below in Table 8.

TABLE 8

| | Thickness of Joint (in cm) | | | | | | |
| --- | --- | --- | --- | --- | --- | --- | --- |
| Groups | 0 hr | 2 hr | 4 hr | 8 hr | 24 hr | 48 hr | 72 hr |
| Phen 1 | 0.47 ± 0.05 | 0.62 ± 0.08 | 0.58 ± 0.06 | 0.61 ± 0.08 | 0.55 ± 0.05 | 0.54 ± 0.05 | 0.52 ± 0.03 |
| Phen 2 | 0.45 ± 0.06 | 0.59 ± 0.03 | 0.56 ± 0.04 | 0.60 ± 0.06 | 0.54 ± 0.05 | 0.52 ± 0.04 | 0.50 ± 0.03 |
| Phen 3 | 0.48 ± 0.04 | 0.59 ± 0.03 | 0.59 ± 0.04 | 0.62 ± 0.06 | 0.52 ± 0.05 | 0.54 ± 0.05 | 0.55 ± 0.05 |
| Phen 4 | 0.49 ± 0.04 | 0.56 ± 0.05 * | 0.56 ± 0.05 | 0.62 ± 0.03 | 0.55 ± 0.05 | 0.53 ± 0.04 | 0.51 ± 0.03 |
| Phen 5 | 0.49 ± 0.04 | 0.56 ± 0.04 * | 0.56 ± 0.04 | 0.62 ± 0.03 | 0.54 ± 0.05 | 0.53 ± 0.05 | 0.51 ± 0.03 |

Note:
Phen 1-Gum Acasia (pacebo); Phen 2-Phenyramidol oxalate(+); Phen 3-Phenyramidol racemate; Phen 4-phenyramidol oxalate(−) and Phen 5-positive control-Diclofenac Values are expressed as mean ± SD. (n = 10).
* Significantly different from vehicle control group (p < 0.05).

Figure 18:
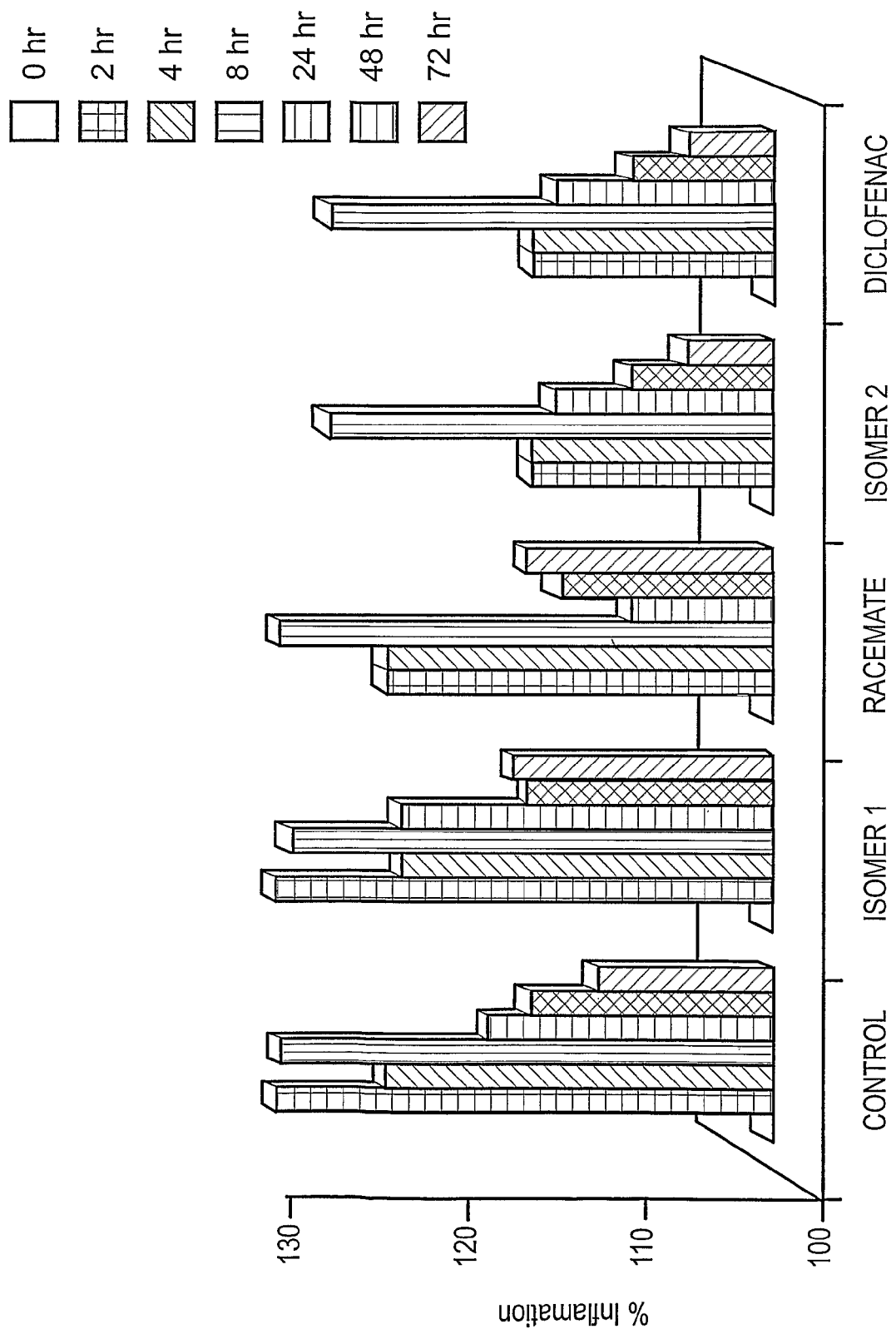
FIG. 18 depicts that the tested formulation (Phen4) shows significant anti-arthritic activity.

The data from the test clearly showed that Phen 4 exhibits significant difference (p<0.05) from normal control (After application of One Way ANOVA followed by Dunnett's Test) at 2 hr. At the same time positive control Phen 5 (Diclofenac), also demonstrates significant decrease in the thickness of the joint. However, other treatment groups showed no significant decrease in thickness of the joint. Thus it can be concluded that the test formulation Phen 4 exhibits Anti-arthritic activity (FIG. 18).

Example 10

Anti-Inflammatory Activity of the Oxalate Salts in Mice

Further, the investigations were carried out to determine the anti-inflammatory activities of the molecule of the present invention. Wistar rats weighing between 160-210 gm were divided into 6 groups of 10 animals each. Group I served as control (Placebo) and receive CMC and Group II & III received anti-inflammatory control (positive control) (Diclofenac & Indomethacin respectively). Group IV to VI were treated orally with test formulations. After 15 min. of drug administration, inflammation was induced by injecting 0.1 ml of freshly prepared 1% carrageenin (in normal saline) into the left hind paw of the rat. The paw volume of the mice was measured by measuring the displace fluid in other hand of plethysmometer.

Human daily dose of 2400 mg (800 mg×3 times) was extrapolated to rats for compound A and human daily dose of 1200 mg (400 mg×3 times) was extrapolated to rats for compound B and C. Indomethacin (15 mg/kg and declofenac (10 mg/kg) was used as reference product. Percent increased in rat paw edema was measured and compare to normal control at each time intervals.

The antiinflammatory activity was assessed plethysmographically using following time points after the administration of carrageenan, 1 hr, 2 hrs, 3 hrs and 5 hrs. The results are shown in Table 9.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A method of treating a subject suffering from skeletal muscle disorders, comprising administering to the subject a pharmaceutical composition comprising the (S) enantiomer of 2-(β-hydroxyphenethylamino)-pyridine (Phenyramidol) having the structure of Formula 1, or a pharmaceutically acceptable salt thereof:

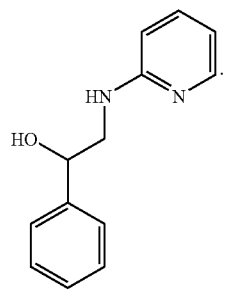

Formula 1

2. The method of claim 1, wherein the composition comprises an oxalate salt of the (S) enantiomer.

3. The method of claim 1, wherein the composition comprises a hydrochloride salt of the (S) enantiomer.

4. A method of treating a subject suffering from skeletal muscle disorders, comprising administering to the subject a muscle relaxant composition comprising the (S) enantiomer of 2-(β-hydroxyphenethylamino)-pyridine (Phenyramidol) having the structure of Formula 1, or a pharmaceutically acceptable salt thereof:

TABLE 9

| | % Increase in Paw volume | | | |
|---|---|---|---|---|
| Groups | 1 HR | 2 HR | 3 HR | 5 HR |
| Phen 2 (T1) | 25.82 ± 11.67 | 40.57 ± 10.07 | 66.59 ± 20.88 | 48.71 ± 15.16 |
| Phen 4 (T2) | 25.37 ± 10.44 | 39.90 ± 6.12 | 68.36 ± 22.20 | 49.65 ± 19.03 |
| Phen 3 (T3) | 24.15 ± 7.27 | 44.73 ± 6.56 | 61.40 ± 18.21 | 47.13 ± 19.14 |
| Phen 1(R1) | 20.07 ± 7.36 | 43.72 ± 6.71 | 65.71 ± 10.59 | 45.85 ± 11.62 |
| Diclofenac (R2) | 15.77 ± 13.94 | 33.39 ± 7.35 * | 43.03 ± 15.41 * | 30.44 ± 9.52 |
| Indomethacin (R3) | 18.58 ± 11.38 | 31.27 ± 4.75 * | 41.42 ± 12.54 * | 28.86 ± 8.22 * |

Note:
Phen 2 is phenyramidol oxalate (+); Phen 4 is Phenyramidol oxalate (−); Phen 3 is Phenyramidol racemate and Phen 4 is piacebo(Gum Acasia). From the above experiments, it has been concluded that the test formulations (Compound T1, T2 and T3) exhibit no antiinflammatory activity.

Formula 1

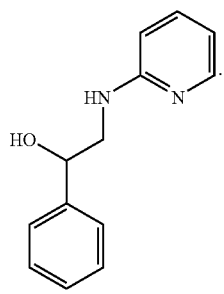

5. The method of claim 4, wherein the muscle relaxant composition comprises the oxalate salt of the (S) enantiomer of 2-(β-hydroxyphenethylamino)-pyridine (Phenyramidol).

6. The method of claim 4, wherein the muscle relaxant composition comprises the hydrochloride salt of the (S) enantiomer of 2-(β-hydroxyphenethylamino)-pyridine (Phenyramidol).

7. The method of claim 5, wherein the oxalate salt of the (S) enantiomer is at least 99% optically pure.

8. The method of claim 6, wherein the hydrochloride salt of the (S) enantiomer is at least 99% optically pure.

* * * * *